US006881363B2

(12) United States Patent
Carlson et al.

(10) Patent No.: US 6,881,363 B2
(45) Date of Patent: Apr. 19, 2005

(54) HIGH THROUGHPUT PREPARATION AND ANALYSIS OF MATERIALS

(75) Inventors: Eric D. Carlson, Cupertino, CA (US); Damian A. Hajduk, San Jose, CA (US); Leonid Matsiev, San Jose, CA (US); Adam Safir, Berkeley, CA (US); Paul Mansky, San Francisco, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/291,108

(22) Filed: Nov. 8, 2002

(65) Prior Publication Data

US 2003/0127776 A1 Jul. 10, 2003

Related U.S. Application Data

(60) Provisional application No. 60/340,884, filed on Dec. 7, 2001.

(51) Int. Cl.[7] .................................................. G01B 1/00
(52) U.S. Cl. ...................................................... 264/40.1
(58) Field of Search ............................... 264/40.1, 349; 209/1; 436/174; 73/863, 432.1

(56) References Cited

U.S. PATENT DOCUMENTS

| | | | |
|---|---|---|---|
| 5,776,359 | A | 7/1998 | Schultz et al. |
| 5,959,297 | A | 9/1999 | Weinberg et al. |
| 5,985,356 | A | 11/1999 | Schultz et al. |
| 6,013,199 | A | 1/2000 | McFarland et al. |
| 6,034,775 | A | 3/2000 | McFarland et al. |
| 6,087,181 | A | 7/2000 | Cong |
| 6,151,123 | A | 11/2000 | Nielsen |
| 6,157,449 | A | 12/2000 | Hajduk |
| 6,175,409 | B1 | 1/2001 | Nielsen et al. |
| 6,182,499 | B1 | 2/2001 | McFarland et al. |
| 6,187,164 | B1 | 2/2001 | Warren et al. |

(Continued)

FOREIGN PATENT DOCUMENTS

| | | |
|---|---|---|
| WO | WO 01/32320 | 5/2001 |
| WO | WO01/33211 | 5/2001 |
| WO | WO 02/081079 | 10/2002 |

OTHER PUBLICATIONS

Copending U.S. Appl. No. 09/667,119, filed Sep. 20, 2000.
Copending U.S. Appl. No. 09/215,417, filed Dec. 18, 1998.
Copending U.S. Appl. No. 09/938,994, filed Aug. 24, 2001.
Copending U.S. Appl. No. 09/939,252, filed Aug. 24, 2001.
Copending U.S. Appl. No. 09/939,263, filed Aug. 24, 2001.
Copending U.S. Appl. No. 09/939,149, filed Aug. 24, 2001.
Copending U.S. Appl. No. 09/939,404, filed Aug. 24, 2001.
Copending U.S. Appl. No. 09/174,856, filed Oct. 19, 1998.
Copending U.S. Appl. No. 09/420,334, filed Oct. 18, 1999.
Copending U.S. Appl. No. 09/580,024, filed May 26, 2000.
Copending U.S. Appl. No. 09/156,827, filed Sep. 18, 1998.
Copending U.S. Appl. No. 09/954,449, filed Sep. 17, 2001.
Copending U.S. Appl. No. 60/340,884, filed Dec. 7, 2001.
Copending U.S. Appl. No. 60/314,842, filed Aug. 24, 2001.
Copending U.S. Appl. No. 10/225,942, filed Aug. 22, 2002.
Copending U.S. Appl. No. 09/633,255, filed Aug. 7, 2000.

(Continued)

*Primary Examiner*—Mark Eashoo
(74) *Attorney, Agent, or Firm*—Dobrusin & Thennisch PC

(57) ABSTRACT

A rapid throughput method for the preparation, analysis or both of libraries of material samples is provided. According to the method, a plurality of samples is provided. Providing the plurality of samples can include a variety of sample formation techniques including, but not limited to, extruding, milling, compression preparation, rotary mixing, microcentrifugation, molding and casting. Preferably, the samples are solidified into a near net shape configuration appropriate for testing of properties or characteristics of the samples.

56 Claims, 13 Drawing Sheets

U.S. PATENT DOCUMENTS

| | | | |
|---|---|---|---|
| 6,225,487 B1 | 5/2001 | Guram | |
| 6,248,540 B1 | 6/2001 | Weinberg et al. | |
| 6,260,407 B1 | 7/2001 | Petro et al. | |
| 6,265,226 B1 | 7/2001 | Petro et al. | |
| 6,371,640 B1 | 4/2002 | Hajduk et al. | |
| 6,393,898 B1 * | 5/2002 | Hajduk et al. | 73/54.05 |
| 6,438,497 B1 | 8/2002 | Mansky et al. | |
| 6,507,945 B1 | 1/2003 | Rust et al. | |
| 6,535,284 B1 * | 3/2003 | Hajduk et al. | 356/367 |
| 6,605,473 B1 * | 8/2003 | Hajduk et al. | 436/174 |
| 2002/0020670 A1 * | 2/2002 | Petro | 210/656 |
| 2002/0148282 A1 * | 10/2002 | Hajduk et al. | 73/54.07 |
| 2002/0160527 A1 | 10/2002 | Cernohous et al. | |
| 2002/0172631 A1 | 11/2002 | Chandler, Jr. | |
| 2002/0190001 A1 * | 12/2002 | Petro | 210/656 |
| 2002/0194930 A1 | 12/2002 | Crosby et al. | |
| 2002/0197732 A1 | 12/2002 | Carnahan et al. | |
| 2003/0068829 A1 * | 4/2003 | Giaquinta et al. | 436/173 |
| 2003/0070988 A1 * | 4/2003 | Petro et al. | 210/656 |
| 2003/0134033 A1 | 7/2003 | Holguin et al. | |
| 2003/0142309 A1 * | 7/2003 | Kuebler et al. | 356/338 |
| 2004/0017896 A1 * | 1/2004 | Hajduk et al. | 378/208 |

OTHER PUBLICATIONS

Copending U.S. Appl. No. 10/177,185, filed Jun. 21, 2002.
Copending U.S. Appl. No. 60/300,792, filed Jun. 25, 2001.
Wang, Meng–Jiao, et al., "Carbon–Silica Dual–Phase Filler, A New–Generation Reinforcing Agent for Rubber. Part VI. Time–Temperature Superposition of Dynamic Properties of Carbon–Silica–Dual–Phase–Filler–Filled Vulcanizates", Journal of Polymer Science: Part B: Polymer Physics, Feb. 4, 2000, pp. 1240–1249, v. 38, John Wiley & Sons, Inc.
Combinatorial Methods at NIST, (Nov. 27, 2000), Draft Paper.

* cited by examiner

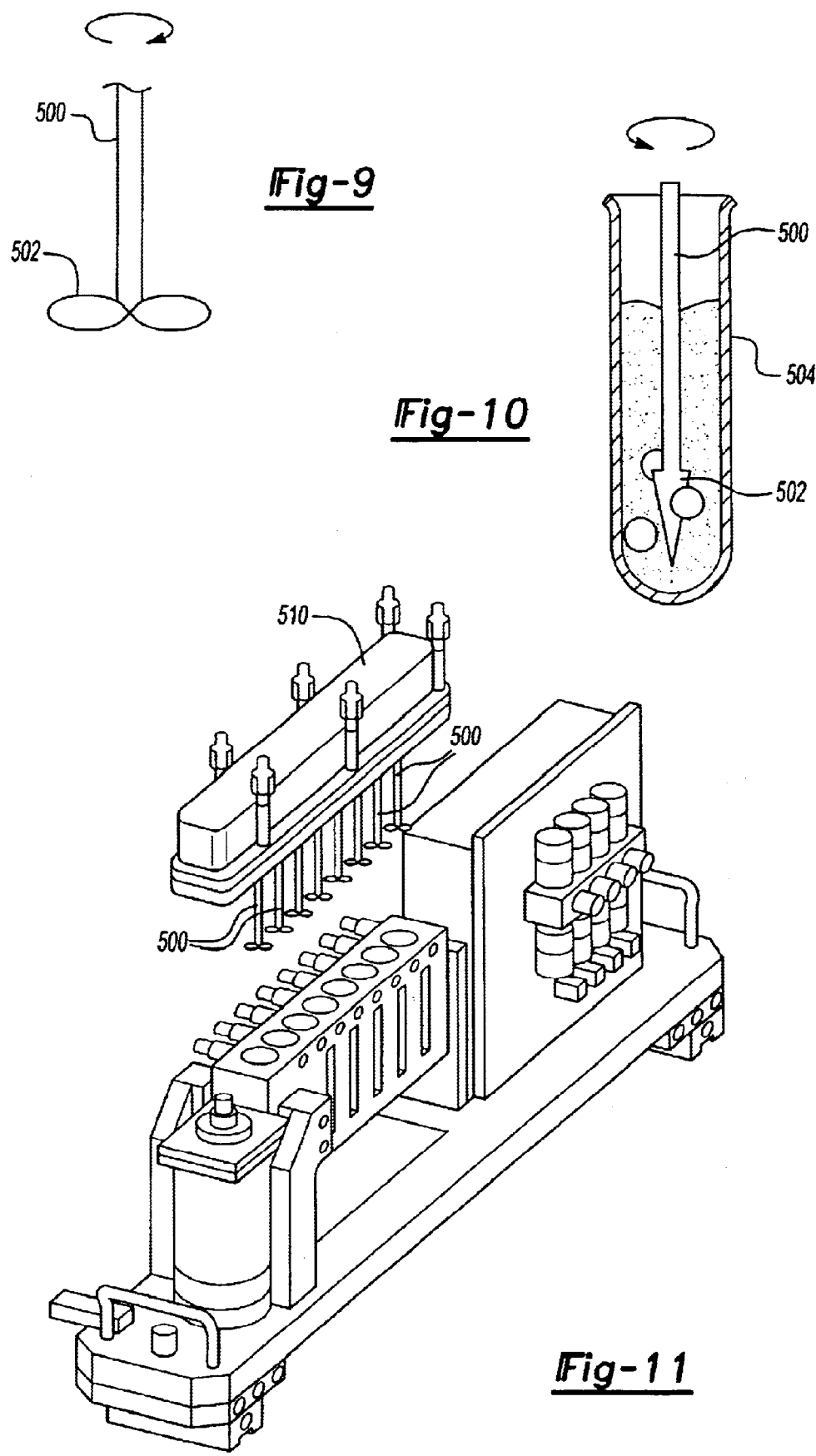

HIGH THROUGHPUT PREPARATION AND ANALYSIS OF MATERIALS

This application of claims the benefit of U.S. Provisional Application No.: 60/340,884 filed Dec. 7, 2001.

FIELD OF THE INVENTION

The present invention generally relates to methods for high throughput preparation and analysis of materials, and more particularly to the high throughput preparation and analysis of libraries of materials for the discovery of new materials or the rapid characterization of existing materials.

BACKGROUND OF THE INVENTION

The discovery of new materials with novel chemical and physical properties often leads to the development of new and useful technologies. Over forty years ago, for example, the preparation of single crystal semiconductors transformed the electronics industry. Currently, there is a tremendous amount of activity being carried out in the areas of new solid materials. Unfortunately, even though the chemistry of extended solids has been extensively explored, few general principles have emerged that allow one to predict with certainty composition, structure and reaction pathways for the synthesis of such solid state compounds, compositions or structures. Moreover, it is difficult to predict a priori the physical properties or the microstructure that a particular material will possess.

Clearly, the preparation of new materials with novel chemical and physical properties is at best happenstance with our current level of understanding. Consequently, the discovery of new materials or materials with desirable properties (e.g., physical properties) can depend largely on the ability to synthesize and analyze new materials, compounds, compositions or structures. For instance, the discovery and formation of materials such as polymers, elastomers and the like may at least partially depend upon the ability to form samples in a format appropriate for testing the physical properties of those samples. As an example, it may be desirable to form combinatorial libraries of samples with a substantially uniform configuration (e.g., having uniform size, shape, surface smoothness or topography) to allow characteristics of the samples to be uniformly tested and for allowing the characteristics of the samples to be meaningfully compared. However, it may be difficult to form samples with various different chemical compositions while maintaining a substantially uniform physical configuration for the samples.

As such, there exists a need in the art for more efficient, economical and systematic approaches for the preparation of materials and for the screening of such materials for information potentially bearing upon the actual useful properties of the materials.

Schultz et al., in U.S. Pat. No. 5,985,356 entitled "Combinatorial Synthesis of Novel Materials" disclose methods for preparing and screening arrays of materials for combinatorial material science applications, and is incorporated herein by reference.

This invention provides methods and apparatus for the formation and testing of combinatorial libraries or arrays of polymer and other materials on or in suitable substrates by effectively utilizing a certain combination of steps or structures. The invention can be used to make known materials or new materials.

SUMMARY OF INVENTION

The present invention generally provides a rapid throughput method for the research and development of materials, including but not limited to homogeneous materials or blends of different materials, wherein the materials include a metal, a polymer, a ceramic, a composite, or another solid material.

According to one embodiment, the method includes the steps of providing a first material; providing a second material; and blending the second material with the first material to form a blend; and optionally forming a material sample of the blend, characterizing the morphology of the blend, characterizing the composition of the blend, screening the blend for at least one property of interest, or a combination thereof. In a particularly preferred embodiment, the steps of blending materials, forming the material samples, or both, are repeated sequentially or performed simultaneously to create a library of a plurality of samples (e.g., at least 4, at least 8, at least 24 or even at least 96). In another particularly preferred embodiment, the methods are performed in miniature scale, such as for preparing samples as small as about 0.1 kg or smaller (e.g., on the order of about 0.001 kg or smaller).

According to another embodiment, the method includes the steps of providing a material sample in at least a partially fluidic state. Thereafter, the samples are solidified into substantially the desired sample shape that is suitable for analysis. Optionally, the sample is characterized in relation to its properties, composition or otherwise.

The present invention advantageously permits for the rapid throughput formation of materials in a format appropriate for rapid combinatorial screening, for rapid discovery of new processing or treatment conditions, for rapid characterization of new or existing materials, or a combination thereof.

DESCRIPTION OF DRAWINGS

FIGS. 9–11 illustrate apparatuses for rotary mixing of materials in accordance with an aspect of the present invention.

DETAILED DESCRIPTION OF PREFERRED EMBODIMENT

Figure 1:
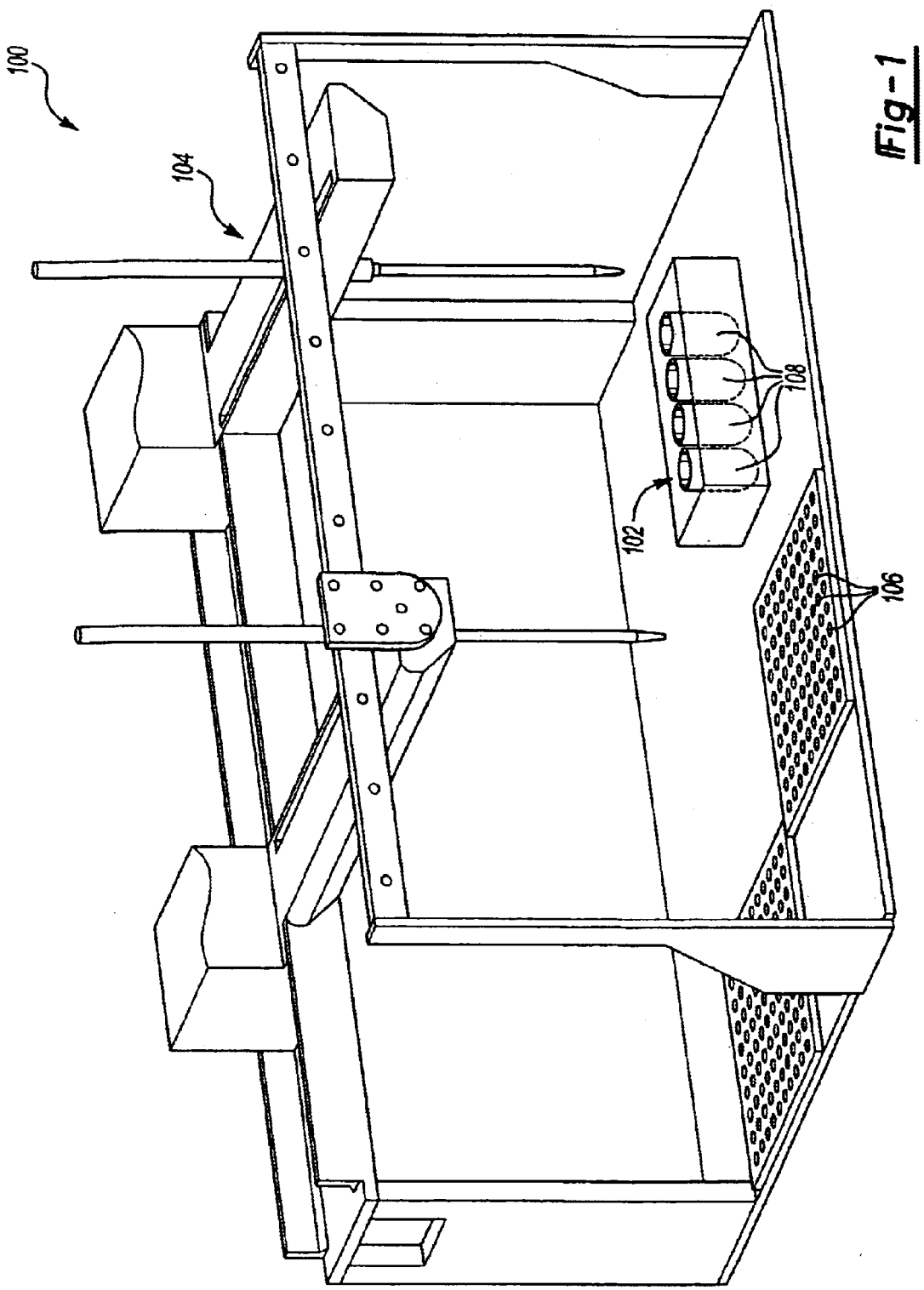
FIG. 1 illustrates a system for providing material samples in accordance with an aspect of the present invention.

According to one aspect, the present invention provides a method for the research and development of commercially attractive materials that, preferably, includes the steps of:

1) Providing a library of at least partially fluidic material samples; and
2) Solidifying the library of material samples into substantially the desired sample shape that is suitable for analysis.

The method in particular makes use of time, evaporation, heat, pressure, vacuum conditions or a combination thereof for achieving the desired resulting configuration.

According to another aspect of the invention, the step of solidifying the library of material samples provides the samples in a format suitable for analysis for determining a characteristic or property of the samples. Alternatively, however, the samples may be used for a variety of other purposes as well.

In yet another aspect, the present invention provides a method for the research and development of commercially attractive blend materials, including the steps of:

1) Providing a first material;
2) Providing a second material;
3) Blending the second material with the first material;
4) Forming a material sample of the blend; and
5) Characterizing the morphology of the blend, characterizing the composition of the blend, screening the blend for at least one property of interest, or a combination thereof.

As used herein the term "blend" shall refer to a mixture of at least two chemically or physically different materials. In a preferred embodiment, but not necessarily required in the practice of the present invention, at least one of the materials is a polymer ("polymers" shall encompass homopolymers, copolymers, oligomers, co-oligomers, polymer blends or the like). Blends herein may be homogeneous, heterogeneous or otherwise. Blends may include two or more materials that are substantially miscible or substantially immiscible relative to each other for a given condition. Blends may include at least two materials that differ in form, composition, processability, surface characteristic, diffusion, morphology, phase separation behavior, or some other characteristic. Moreover, such characteristics may render the materials immiscible or miscible relative to each other and/or compatible or incompatible relative to each other. Blends of the present invention may be mono-phase or may take any of a number of different multi-phase forms, examples of which include dispersions, composites with other polymers, interpenetrating networks, or the like. Blends may also include polymer alloys that include a modified interface between polymers. The different materials in a blend need not be compositionally distinct to form a blend; however, blends will, in most instances, include at least two materials of different architecture.

In a particularly preferred embodiment, the method of the present invention is employed as part of a research and development program for the discovery or optimization of materials that are made in bulk quantities (e.g., greater than about 10 kg, more preferably greater than about 100 kg, still more preferably greater than about 1000 kg, and still more preferably greater than about 10,000 kg), such as that amount sufficient for meeting commercial or industrial demands.

As the following will illustrate, the invention involves various aspects that, independently or in combination, may contribute to this result, or conversely, the elimination during research and development of certain materials from consideration for bulk production. For example, in one aspect, the present invention is directed toward methods for the physical mixing of two or more materials for forming a blend composition. In another aspect, the present invention is directed to methods for the formation of material samples (e.g., of a single material, or blends of plural different materials) that are suitable for quantitative or qualitative analysis. In yet another aspect, the present invention is directed to methods for the analysis of material samples. Further aspects will be ascertainable from review of the discussion herein. As will be appreciated, some of the methods disclosed herein may be employed for either or both of forming a blend of plural different materials by mixing or forming material samples of one material or a plurality of different materials. Thus, discussion herein of a method in one context is not intended to exclude application of the method in another context. Further, it will be appreciated that material samples or blends prepared in accordance with the methods herein may be subjected to additional art-disclosed processing techniques, such as thermal exposure, surface treatment or the like.

One unique feature of the present invention is the ability to employ the methods for the preparation of miniature scale material samples, thereby enabling rapid throughput analysis and cost-effective use of equipment, materials and other resources.

Materials

The present invention may be useful for forming and screening combinatorial libraries chosen from a wide variety of materials, including but not limited to, metals, ceramics, composites, organic materials, inorganic materials, flocculated materials, colloids, non-volatile materials, soluble materials, combinations thereof and the like. Other materials appropriate for combinatorial research may include, for instance, catalysts, products of various polymerization reaction conditions, lubricants, gels, adhesives, coatings and/or products of new post-synthesis processing conditions. Materials appropriate for combinatorial research according to the present invention may be also selected from foodstuffs, cosmetics, beverages, lotions, creams, pharmaceuticals, inks, body fluids, fuels, additives, detergents, surfactants, shampoos, conditioners, other hair styling products, dyes, waxes, fuel cell electrolytes, photoresist, semiconductor material, wire coatings, or the like.

According to one highly preferred aspect, though applicable to other materials, the present invention has been found particularly useful in connection with the processing and testing of, amongst other materials, polymeric materials or blends including the same. In this regard, the present invention can be employed to investigate any of a number of different types of materials including homogeneous blends, heterogeneous blends, interpenetrating networks, copolymers, composites, or other materials. Preferably, the blends will include a first material and a second material, one or both of which may be polymers. The blends need not be homogeneous materials or homogeneous polymer materials, and may include, for instance, organic or inorganic constituents. Further, the blends may be of non-polymers, inorganic materials, organic materials, biological materials, pharmaceutical compounds and polymorphs thereof, salts of small organic molecules or other non-biological or biological materials.

Without intending to be limited thereby, the present invention is contemplated for use in connection with research or other activities addressing thermoset polymers, thermoplastic polymers, or mixtures thereof. The polymers also may be thermosets that become crosslinked. For example, among the popular industrial polymers for which the present invention is useful are polymers selected from one or more types of polymers including, for example, polyolefins (e.g., polyethylene, polypropylene, polyethylene terephthalate, or the like), vinyls (e.g., polyvinyl chloride), polyamides (e.g., NYLON®), polyimides, polyurethanes, acrylics, polyesters, celluloses, acetates, melamines, thermoplastic rubbers, thermosetting rubbers, fluorocarbons (e.g. PTFE or TEFLON®), polystyrenes, nitrites, phenolics, polycarbonates, epoxies, ABS, polyethylene ether ketones, acetals, or otherwise. The polymers may be high molecular weight, medium molecular weight, low molecular weight, high density (HD), low density (LD) or medium density (MD), conductive polymers, insulative polymers, ionomers or the like.

Examples of other polymeric materials may include various polyolefin resins, mixtures of polylefins with other thermoplastics, mixtures of polyethylene (e.g., LDPE, VLDPE, or HDPE), polypropylene, ethylene/α-olefin copolymer, and/or polybutene-1 with ethylene alkyl (meth) acrylate copolymers, ionomers, nylon and polycarbonates. Other particularly attractive materials may include, for example, a polyolefin selected from poly(4-methylpentene-1)(PMP), 4-methylpentene-1 (4-MP-1)/decene-1 copolymer, polybutene-1 (PB), ultra-high molecular weight polyethylene, high density polyethylene or combinations thereof.

In some instances, it is possible that the polymer materials prepared or analyzed in accordance with the present invention may be substantially pure; that is consisting essentially of constituent polymers. However, the present invention also lends itself well to the preparation and analysis of polymer materials that include additional ingredients, such as additives (e.g., light or temperature stabilizers, performance enhancers, biocides, fungicides, flame retardants, impact modifiers, foaming agents, or the like) colorants, reinforcements (e.g., fibers, particles, rovings, mats, foams, or the like, which may be any suitable composition such as carbon, aramid or otherwise).

In this regard, as with other applications discussed herein, it is contemplated that the conditions under which the methods of the present invention are employed may be varied in an effort to replicate temperature, time, pressure or other conditions to which the material material samples may encounter in a commercial or industrial environment.

In general, though one aspect of the present invention contemplates rapid formation, synthesis and/or characterization of individual material samples in isolation, the method and system of the present invention preferably contemplates forming a library of a plurality of same or different materials using rapid-serial synthesis techniques, parallel synthesis techniques or a combination thereof. In the formation of libraries in accordance with the present invention, one or a plurality of ingredients may be selected to form a desired material or may be selected to explore a compositional or process parameter range or phase space potentially useful as a desired material.

It will be appreciated that materials also contemplate different materials having the same composition, such as isomers, polymorphs, or being selected of different molecular weights, polydispersities, weight distributions, chain branching or the like. It will also be appreciated that many parameters can be altered to produce a wide range of materials, such as the number of different component ingredients, the relative amounts of each component, the co-monomer content of a component, the nature and extent of chain branching or the like. The component ingredients may be the product of a single reactor or plural reactors (e.g., a tandem, serial reactor for producing bimodal molecular weight distribution polymers).

Providing Libraries of Material Samples

In general, libraries of material samples may be provided in a variety of forms for processing (e.g., solidification, formation and the like) and testing (e.g., screening, property determination and the like). Samples may be provided as fluids, solids, partial fluids, gasses, liquids, partial solids or a combination thereof. According to one aspect, each of the samples of a library is at least partially fluidic prior to further processing of the samples or may be a liquid suspension or solution. According to another aspect, involving polymer materials, a library of samples may be provided wherein each of the samples is at least a partially, if not substantially entirely homogeneous liquid solution that includes one or more polymeric or other materials and a solvent. According to still another aspect of the invention, a library of samples may be provided wherein each of the samples is a liquid suspension or solution that includes one or more polymeric or other materials that are supplied at a temperature above the melting point or glass transition temperature. Such samples may be heated or otherwise induced to at least partially melt or liquidize or the samples may be at least partially liquid at room temperature or other ambient conditions.

In a highly preferred aspect of the invention, the formation of samples contemplates an optional first step of forming a material (e.g., forming a blend of a material, such as by mixing), and a second step of preparing samples for analysis from the material. While these steps may be performed separately, as will be seen herein, it is also possible to combine them into a single step. The samples may take any suitable form for the analysis to be applied to it. Thus, the samples may be films, fibers, droplets, rings, plates, ribbons, or the like. Other shapes will be apparent from the discussion herein.

Moreover the samples may be formed in a variety of sizes and weights, though to benefit from and facilitate the various advantages of the invention, it is preferable that the techniques of the present invention be employed in miniature scale, as compared with conventional blend sample preparation and testing techniques. For example samples may have thicknesses as low as about 0.1 micron to about 25 mm. Moreover, exemplary ranges of weights for samples include ranges of about 1 microgram to about 0.5 kilogram, more preferably about 1 mg to about 100 mg and even more preferably about 10 mg to about 80 mg.

The formation of blend materials thus generally employs one or a combination techniques such as liquid blending, melt blending, mixing, or other blending techniques.

Libraries of a plurality of sample materials may be formed according to a variety of protocols and may be formed automatically or manually. According to the present invention, one or more systems, methods or both are used to assist in dispensing various components for forming libraries of material samples. Though manual or semi-automated systems and methods are possible, preferably an automated system or method is employed. A variety of robotic or automatic systems are available for automatically or programmably providing predetermined motions for handling, contacting, dispensing, or otherwise manipulating materials in solid, fluid, liquid or gas form according to a predetermined protocol. Exemplary robotic systems are commercially available from CAVRO Scientific Instruments (e.g., Model NO. RSP9652) or BioDot (Microdrop Model 3000). It should be appreciated that, as addressed herein, libraries may comprise an array of plural materials on a single substrate, but it is not limited thereto. For instance, a library may comprise a plurality of materials on different substrates.

According to one aspect, for forming a plurality samples including a polymer, the samples may be provided to a substrate by dispensing one or more solvents to various regions of a substrate followed by dispensing one or more polymeric or other materials to the regions to intermix and form a library of sample solutions. Preferably, the solvents are dispensed as liquids. The polymeric or other materials may be dispensed as solids, liquids or a combination thereof and may be dissolved or dispersable (e.g., soluble) in the solvents with or without the use of elevated temperatures. According to another aspect, samples may include only one or more polymeric materials, which may be dispensed to a substrate as solids, liquids or a combination thereof. Thus, it is possible that a sample is dispensed as a solid and then is rendered in a liquid state.

According to another aspect, the present invention contemplates the use of any suitable technique for mixing at least two materials together to form a blend. In one embodiment, in general, two or more materials are provided and energy is applied to physically blend the materials together. How the energy is applied, and any means for minimizing the amount of energy necessary will typically vary from application to application. Typically, however, the energy is applied by a mechanical mixing, and more preferably by mixing that imparts shear flow, elongational flow or a combination thereof to the mixed materials. Examples of such mixing include, without limitation, periodic mixing (e.g., by rotating or oscillating a mixing arm), forcing the materials through a constricted volume (e.g., between opposing surfaces, such as the nip and roll of a mill, the screw and barrel of an extruder, a wall defining an orifice or the like), or other suitable pressure or force application. The starting materials may be provided in any suitable form. For example, they may be provided as a block, a plate, a bale, a sheet, a rod, a fiber, a powder, a pellet, a fine particulate, a granule, a solution, a fluid, a melt, an emulsion or dispersion or the like.

According to still another aspect, mixing may be assisted or accomplished by one or more wet chemistry techniques. For example, the materials may be mixed in solution, a latex or other dispersion, or another liquid state. In one preferred embodiment, the materials are mixed using art-disclosed co-solvent techniques. Thus, at least one of the materials, and preferably all of them, are dissolved in a common solvent with the materials to be mixed. After such dissolution (which may be facilitated optionally at elevated temperature), the solvent is evaporated or otherwise removed, with the resulting mixture being cast (e.g., film cast), dried (e.g., by freeze drying, elevated temperature drying, the use of a desiccant or other drying agent, spray drying, or another suitable drying treatment). Blends may also be co-precipitated from solution with the addition of an anti-solvent. The solid blend may then be separated from the liquid medium, such as by decanting the liquid and filtering the solid samples.

In another embodiment, it may be possible to form an interpenetrating network using suitable art-disclosed techniques. For example, a suitable monomer might be employed as a solvent for another polymer. Polymerization thus leads to defining the interpenetrating network.

Mixing may take place at any suitable temperature. In one aspect of the present invention, in the context of a polymer containing material, it is preferred that any mechanical mixing occurs at or above the glass transition temperature (and more preferably at or above the melting point) of at least one and preferably all of the polymer materials being mixed.

Referring to FIG. 1, there is illustrated one exemplary system 100 for dispensing samples, blending materials and the like. The system 100 includes one or more sources 102 of material samples, and a dispensing apparatus 104 (e.g., a Cavro fluid dispensing robot) for transferring the material samples to a suitable substrate 106 or other surface or container on or in which the material samples are brought into contact. By way of illustration, in one embodiment, a sample is provided as a liquid within receptacles 108 (which optionally are integrated in a single structure, such as a microtiter plate).

The dispensing apparatus 104 may be operated manually. Preferably it is automated and is in controlling communication with a computer or other suitable programmable controller, and is directed to aspirate fluids from the receptacles 108 in predetermined amounts and then to deliver the fluids to the substrate 106. For example, the dispensing apparatus will receive instructions from IMPRESSIONIST™ software, based upon information inputted by a user through LIBRARY STUDIO®, where a library is initially designed.

Where samples have more than one ingredient or other components, the components may be mixed before, during or after deposition onto the substrate. In this regard, there might be an intermediate stage, substrates or receptacles employed for mixing, from which mixed component are then dispensed to the substrate 106. Further, it is possible that the substrate 106 functions as a further processing site, at which solid material samples are formed, analyzed or both.

In one embodiment of the invention, polymer samples are dissolved in a solvent, for rendering the sample and solvent together in a solution. The respective solutions are combined with each other for forming a material sample into a common solution. Optionally, before combining, the components (which preferably differ from each other) of each of the samples will include a similar solvent relative to the other. Thus, upon combining, the ingredients share a single common solvent. Of course, different respective solvents alternatively might be employed. It may also be possible that the samples are suspended in a liquid medium, rather than dissolved therein. The present liquid blending techniques might also be employed in combination with one or a plurality of other blend formation techniques, such as those disclosed herein. Additionally, it is possible that chemical reactions for reactive blending may be employed. Liquid blending techniques might also be employed in combination with one or a plurality of other blend or other sample formation techniques, such as those disclosed herein. Additionally, it is possible that chemical reactions for reactive blending or formation may be employed.

Once combined and dispensed on the substrate 106, solid blend or other materials can be obtained for analysis from the liquids. Some or all of the liquids might also be separately analyzed in the liquid state, in addition to or alternatively to the solid state testing. Suitable techniques for obtaining the solids include evaporation or drying techniques (e.g., freeze drying or the like), precipitation, filtration or the like.

Miniature Extruder Mixing

Figure 2:
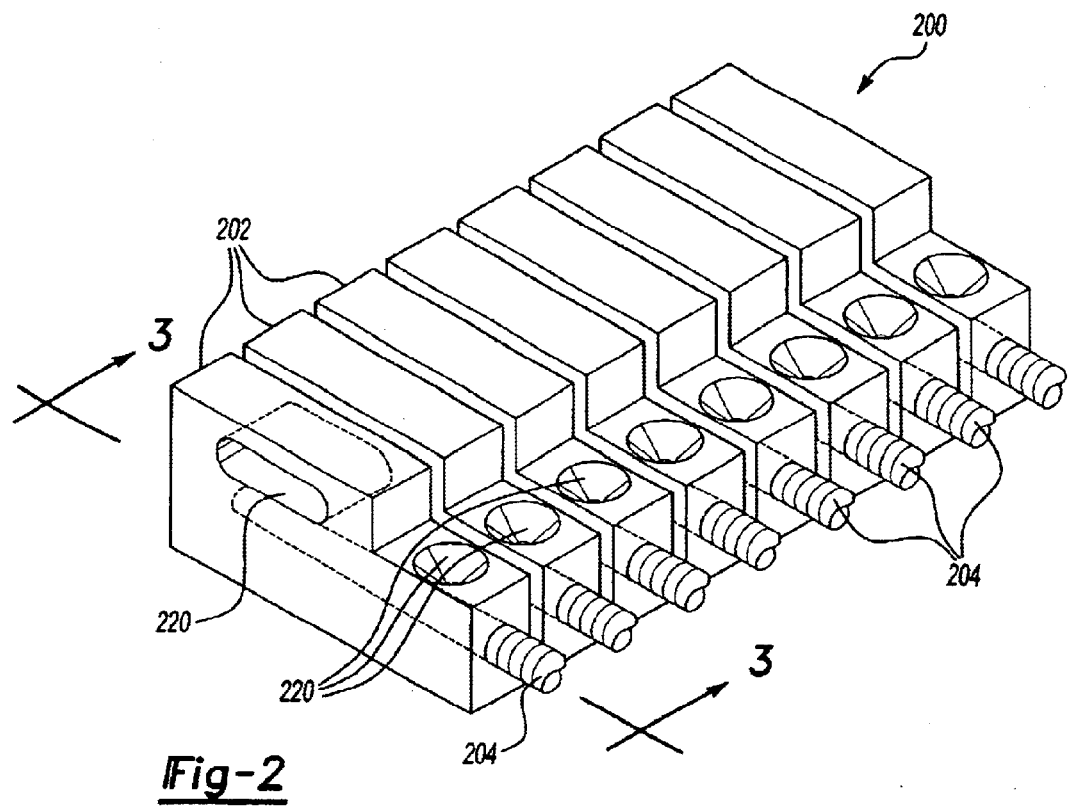
FIG. 2 illustrates a perspective view of a miniature extruder-type mixing apparatus in accordance with an aspect of the present invention.
Figure 3:
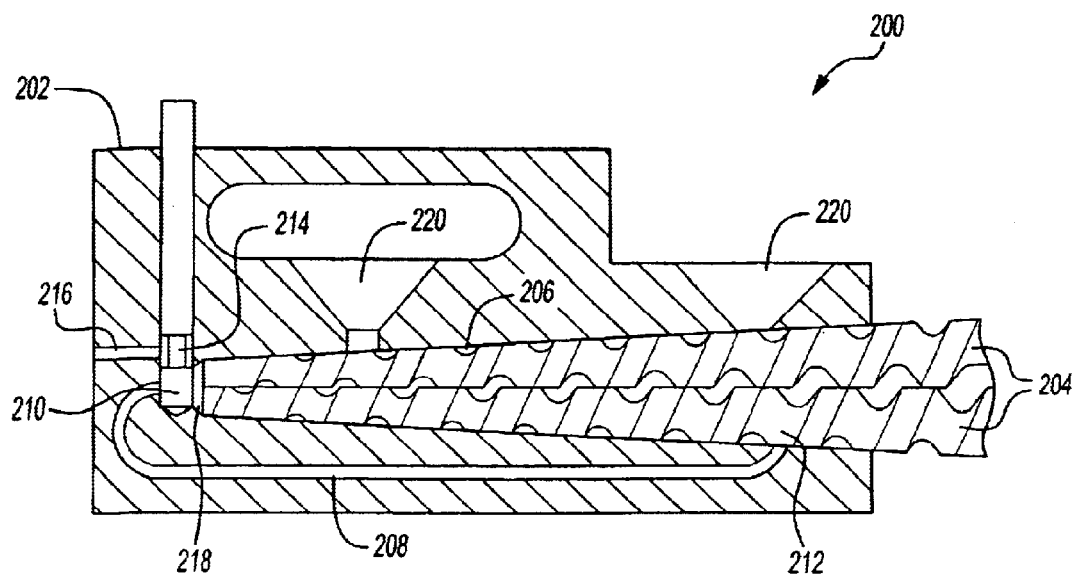
FIG. 3 illustrates a sectional view of the miniature extruder-type mixing apparatus of FIG. 2 taken along line 3—3.

Turning to FIGS. 2 and 3, there is illustrated one example of forming a sample, e.g., a blend that involves the physical mixing of one, or more preferably at least two materials by the use of a suitable miniaturized mixer. By way of example, in one preferred apparatus 200, the miniaturized mixer is a miniature extruder 202, and more preferably is a co-rotatable or counter-rotatable plural screw extruder, having at least two screws 204 that are housed in a common barrel 206. The barrel is preferably a split barrel for facilitating cleaning between material sample runs. Optionally, the barrel has a recirculation channel 208 defined for transporting material in the barrel 206 from a first region 210 to a second region 212 for permitting further mixing. A suitable valve 214 may be employed (e.g., between the screws and an exit outlet 216) for switching between modes of recirculation only, extruding only or a combination thereof.

Though larger systems are possible, the capacity of the screws preferably is less than about 200 $cm^3$, more preferably less than about 75 $cm^3$, still more preferably less than about 25 $cm^3$, even still more preferably less than about 10 $cm^3$, and yet still more preferably on the order of about 5 $cm^3$. The length ("L") of the mixer preferably is less than about 65 cm and more preferably is less than about 35 cm. In one preferred embodiment, the thread of the screws is shaped to have a generally frusto-conical mixing portion 218. They may be configured otherwise, as well, such as having a substantially cylindrical mixing portion. At least one opening 220 is typically provided at one or more upstream location for introducing material to the extruder.

The screws are preferably driven by a suitable motor (not shown), and in one embodiment, a suitable controller (not shown) or suitable software is employed for controlling and varying screw rotation speed as desired, e.g., up to about 1000 rpm, more preferably up to about 400 rpm and still more preferably up to about 200 rpm. In a particularly preferred embodiment, the screw rotation speed is controllable by the user and through input based upon library or material sample design criteria that has been inputted. A suitable axial load measurement device, torque measurement device or both can be also employed for providing feedback to the user about processing conditions. Optionally, the mixing apparatus also is equipped with a suitable temperature monitoring or control device for adjusting screw temperature, barrel temperature or both, for assuring (in combination with the heat generated in situ from the shear of mixing) molten conditions are met before the material exits the apparatus.

An example of one suitable miniaturized mixer is that available commercially from DACA Instruments, under the designation MICROCOMPOUNDER. It is also possible to employ an apparatus having a single screw for mixing.

In operation, as seen in FIG. 3, material is introduced into the apparatus through the opening 220. The rotating screws 204 mix the material thoroughly and advances the material along the length of the barrel 206. Control over the valve 214 will determine whether the material will be permitted to exit through the outlet 216 or be recirculated to an upstream location for further mixing. In this manner, thorough mixing of relatively small amounts of blend ingredients can help be assured prior to exiting as a molten material. Upon exiting, the material may be continuously extruded or extruded intermittently. It may also be extruded into a mold cavity for molding of a material sample. An opening 220' can be used for devolatilization of the mixtures, for introducing materials or a combination thereof.

It will be appreciated that the materials introduced into the apparatus may be in any suitable state. In one embodiment, the materials are introduced in a liquid medium (e.g., as a solution, dispersion, suspension, or the like), with liquid being removed (e.g., by evaporation or otherwise) during the mixing. In another embodiment, the materials are introduced as solid bodies (e.g., as powders, pellets, or the like). Combinations of the above or other techniques are also possible. Thus, it is seen an example of how the above-discussed liquid mixing techniques might also be employed in combination with the present mixing technique to form a blend material in accordance with the present invention.

Milling

Materials, and particularly blends, may also be formed according to the present invention by physically mixing a material, and more preferably at least two materials using a suitable milling operation. In accordance with such milling operation, there is typically provided at least one moving surface and a second opposing surface that is stationary or moving. The opposing surfaces are spaced apart a desired distance so that the moving surface is capable of advancing material through an opening defined between the opposing surfaces. The speed of the moving surface, the width ("w") of the opening (see, e.g., FIG. 5), or both are variable to assure that suitable pressure can be applied to the materials to be blended for blending to occur.

Figure 4:
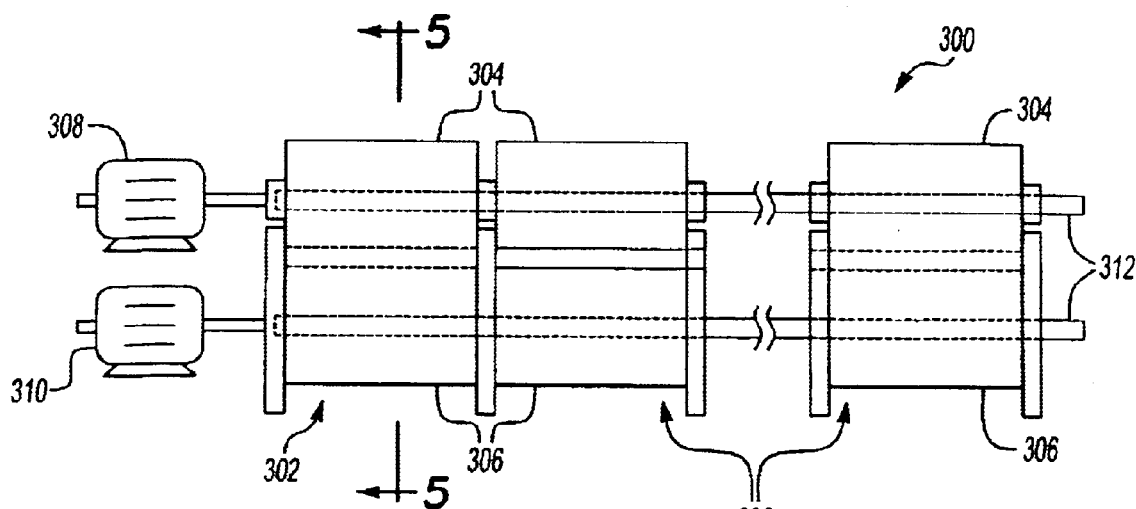
FIG. 4 illustrates a schematic diagram of a milling apparatus in accordance with an aspect of the present invention.
Figure 5:
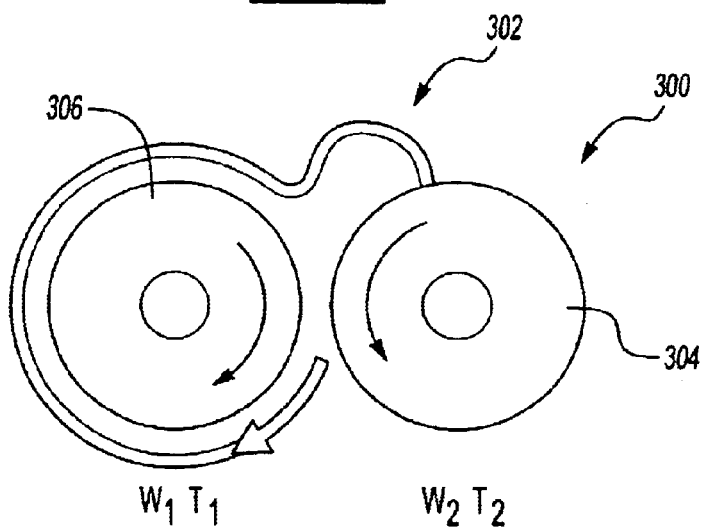
FIG. 5 illustrates a sectional view of the milling apparatus of FIG. 4 taken along line 5—5.

As an example, FIGS. 4 and 5 show an example of molten mixing involving the employment of milling, and preferably a calender milling operation. A milling apparatus 300 is employed, and includes one or a plurality of roller assemblies 302. Each roller assembly 302 includes at least one first roller 304 (e.g., a cylinder) that is positioned in opposing spaced relation (which spacing may optionally be adjustable) to another suitable stationary or movable work surface, and preferably an opposing second roller 306. At least the first roller 304 is rotatable relative to the work surface by a suitable first motor 308. Feed material is introduced between the first roller 304 and the work surface and a resulting force is applied as the material is advanced through the space.

In a particularly preferred embodiment, the first roller 304 is a first cylinder and the opposing work surface is the exterior of the second roller 306, preferably a second cylinder. The first and second roller may be the same dimensions or they may be different. They are both preferably driven by at least one motor, optionally with a suitable differential torque transmitter. They are illustrated here as each being driven by their own respective motor, namely the first motor 308 and the second motor 310. In this manner the relative rotational speeds ($\omega_1$, $\omega_2$) of the rollers may be varied as desired. Further, the respective rollers (or work surface) are each preferably equipped with an independent or common temperature adjuster 312 for permitting the same or different variable temperatures ($T_1$, $T_2$) between the respective rollers (or work surface). By controlling the relative speeds and temperatures of the rollers, it is possible to control the amount of shear or extensional deformation in the materials that pass in the space between them. It also advantageously allows for devolatilization of the materials. In a highly preferred embodiment each of the rollers is divided into plural sections for permitting the simultaneous mixing of plural different blends. Thus, this device may be operated in either or both of shear or elongational deformation modes.

As with the miniature extruder mixing system, discussed above, it will be again be appreciated that the materials introduced into the apparatus may be in any suitable state. In one embodiment, the materials are introduced in a liquid medium (e.g., as a solution, dispersion, suspension, or the like), with liquid being removed (e.g., by evaporation or otherwise) during the mixing. For example, for a polymer solution, a robot such as a Cavro robot, under control of software, such as IMPRESSIONIST™, will direct dispensing of the solution onto a roller that is elevated in temperature, sufficient to evaporate the solution and leave a resulting polymer layer or film. In another embodiment, the materials are introduced as solid bodies (e.g., as powders, pellets, or the like). Combinations of the above or other techniques are also possible. Of course, the above-discussed liquid mixing techniques might also be employed in combination with the present mixing technique to form a material in accordance with the present invention.

The spacing between the rollers may be varied as desired. In one embodiment the spacing is less than about 2 cm, more preferably less than about 1 cm, still more preferably less than about 3 mm, and still more preferably less than about 1 mm.

Figure 6:
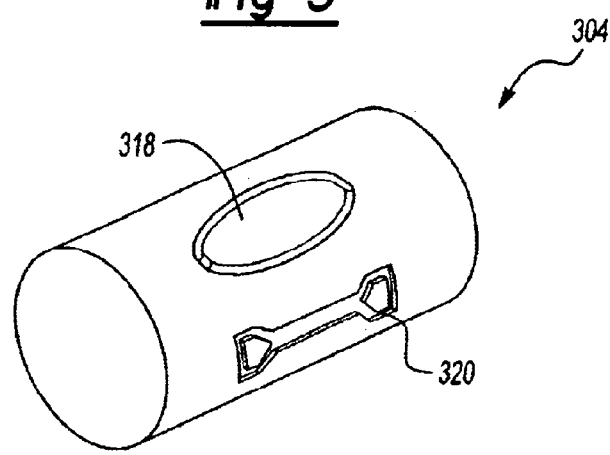
FIG. 6 illustrates a perspective view of an exemplary roller for use in a milling apparatus such as the apparatus of FIG. 4.

In yet another embodiment, shown in FIG. 6, it is possible to prepare material samples by varying the surface topography of a roller surface. For example, one roller (e.g., a third roller) might have a pattern 318 engraved or otherwise defined on it for molding, cutting, embossing or otherwise achieving a desired individual material sample shape. For instance the pattern can be formed in a roller surface having one or more suitable depths (e.g., on the order of millimeters, and preferably less than about 10 millimeters, more preferably less than about 3 millimeters and possibly less than 0.1 millimeters). The pattern might be circular, annular, polygonal, or a combination thereof. Likewise, it might take the form of a suitable shape for the desired test to be performed, e.g., the shape of a tensile bar or other suitable mechanical test piece 320, elliptical ring, plate, or the like. As apparent from FIG. 6, a combination of different shapes could be defined on one or more rollers, to permit a plurality of different material sample shapes to be formed from a single material sample batch.

The skilled artisan will appreciate that the present mixing techniques also may be combined in simultaneous or consecutive relation to each other. Thus, for example, it might be possible to extrude a material sample onto one of the rollers for further mixing or for forming a desired material sample shape.

Further, as indicated above, while FIGS. 4 and 5 illustrate the general concept of using two opposing rolls, it may be possible to omit one of the rolls in favor of a stationary surface spaced opposite the outer surface of the remaining roll. Or, it might be possible to include one or more additional upstream or downstream rolls.

Compression Preparation

Figure 7:
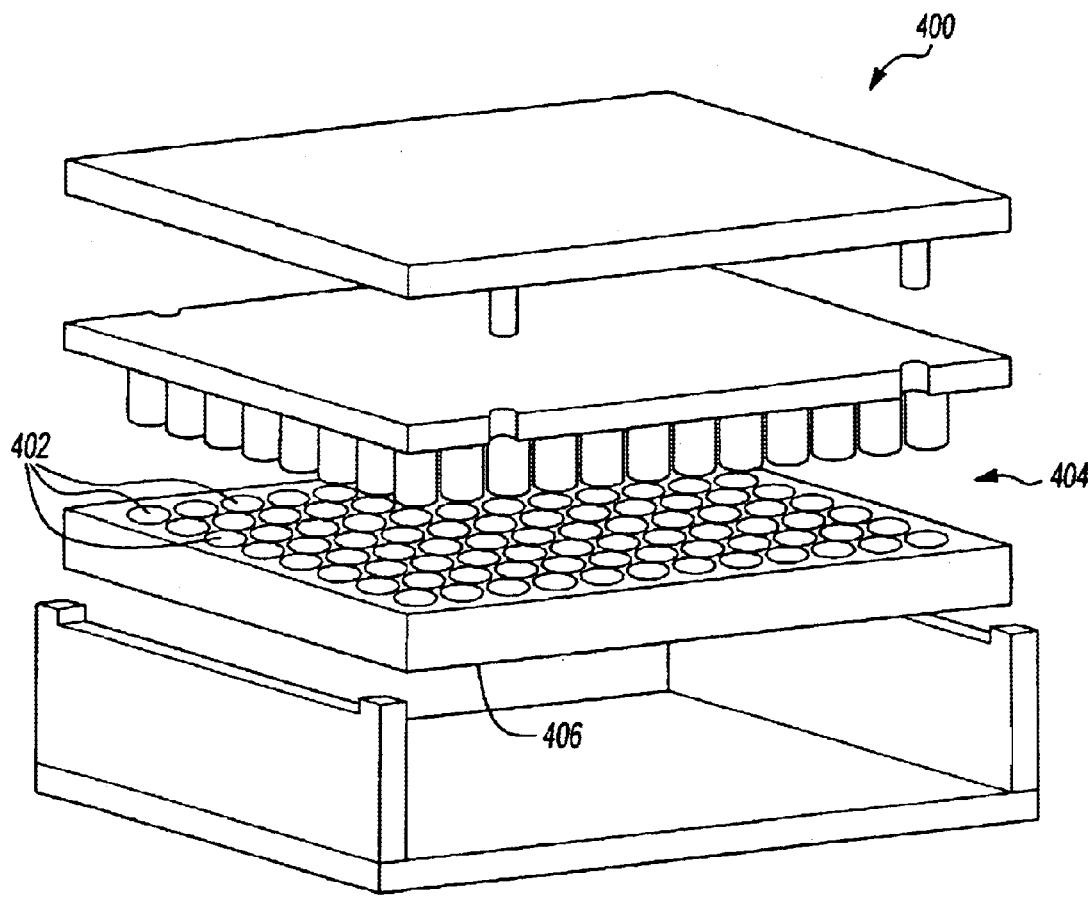
FIGS. 7 and 8 illustrate diagrams of apparatuses for molding material samples in accordance with an aspect of the present invention.
Figure 8:
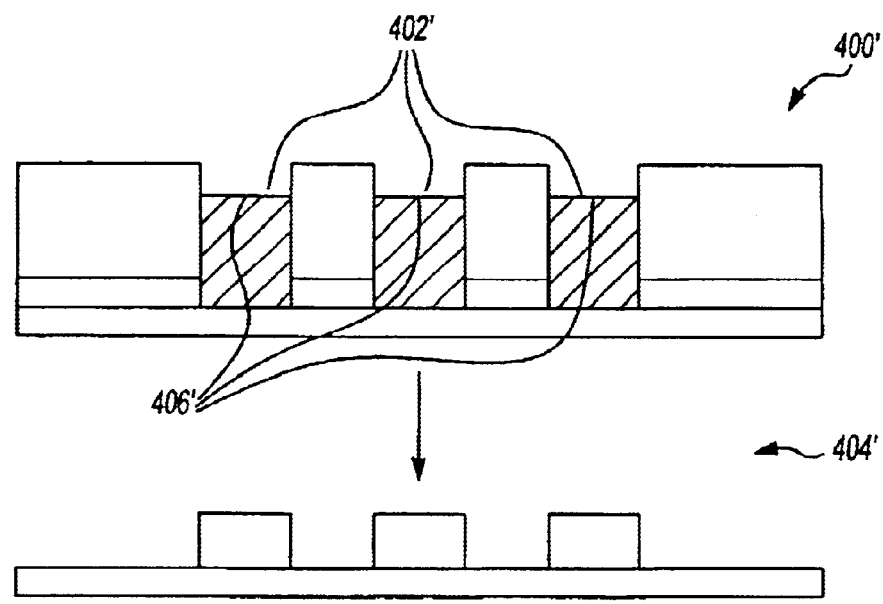

In FIGS. 7 and 8 there are illustrated yet other examples of an apparatus 400 (400') for preparing material samples (blends or other materials) by the application of a force. In this example, the materials are provided in wells 402 (402') of a suitable substrate 404 (404'). As seen in FIG. 9A, the wells may have a fixed wall 406, or the wells may be through-holes (e.g., bores through a block) with a separable wall. A piston or like member having a face is inserted into a well and pressure is applied to compress the materials to be mixed or substantially prepared. It is also possible that two or more pistons are brought into opposing relationship with each other with material disposed between them. The application of pressure thus results in the formation of disc-like material samples. Of course, the above is illustrated by reference to the use of cylindrical wells and pistons, but the shape may vary as desired depending upon the resulting desired material sample shape. For example, the shape may be polygonal, elliptical, oval, or the like, and the piston or opposing surface may be configured for achieving cutouts (e.g., through holes) within the material sample. Moreover, samples may be compressed into engraved cutouts in portions of the substrates. Generally, this method is useful primarily for sample preparation. However, some mixing may result from use, and may advantageously facilitate the formation of blend materials.

Rotary Mixing

Other approaches to mixing blends or other materials, such as rotary mixing may be employed in addition to (e.g., with liquid blending techniques) or alternatively to the above. In general, these will be selected from rotary mixing in the presence of a solvent or the substantial absence of a solvent, or a combination thereof. Referring to FIG. 9, under any of the approaches, typically a rotor shaft 500 is driven manually or by a suitable motor. Along the shaft there will be a projection 502, such as a blade, an arm or the like, which rotates with the shaft and which will contact the material to be mixed for relatively high-torque stirring.

The rotor shaft is placed relative to the material to be blended so that the projection 502 contacts the material. To assist in this, preferably the material is provided on a suitable surface or in a suitable receptacle or container. By way of example, in FIG. 10, there is shown a vial 504 for holding the material. In one particularly advantageous embodiment, a material sample is obtained from a suitable reactor, such as Parallel Polymerization ReactorTM, disclosed in Ser. No 09/826,606, incorporated by reference. The material sample may be dispersed with or without a solvent.

Of course, the above is not intended as limiting. Other mixing techniques may be employed in like manner. For example, in another embodiment, a magnetic stirrer may employed in lieu of or in addition to the rotor shaft. Beads, pellets or the like might also be included in the mixture to increase the mixing shear, elongation or both per unit volume.

Though not necessary in every instance, rotary mixing in the presence of a solvent will typically also include a step of solvent removal. For example, before, during or after mixing, the solvent will be evaporated (e.g., by allowing to sit, by heating, by drying, by applying vacuum, or the like).

Whether rotary mixing is in the presence of a solvent or not, the material to be mixed may also be subject to thermal treatment (e.g., heating, cooling or a combination) to assist in the mixing process. For example, each of the material samples may be individually supported in a substrate having control over temperature for the entire substrate, or for only portions thereof. Of course, any suitable substrate may be employed.

In one embodiment, as seen in FIG. 11, a common manifold 510 holds a plurality of rotor shafts 500. In another, the rotor shafts are supported separately. In another embodiment, each rotor shaft is driven by its own motor. In yet another embodiment, plural shafts are driven by the same motor. A single shaft driven by a single motor may also be employed for high throughput mixing of plural material samples. In the above manner, it can be seen how the present invention advantageously can be employed in parallel formats as well as rapid-serial formats.

Microcentrifugation

Figure 12:
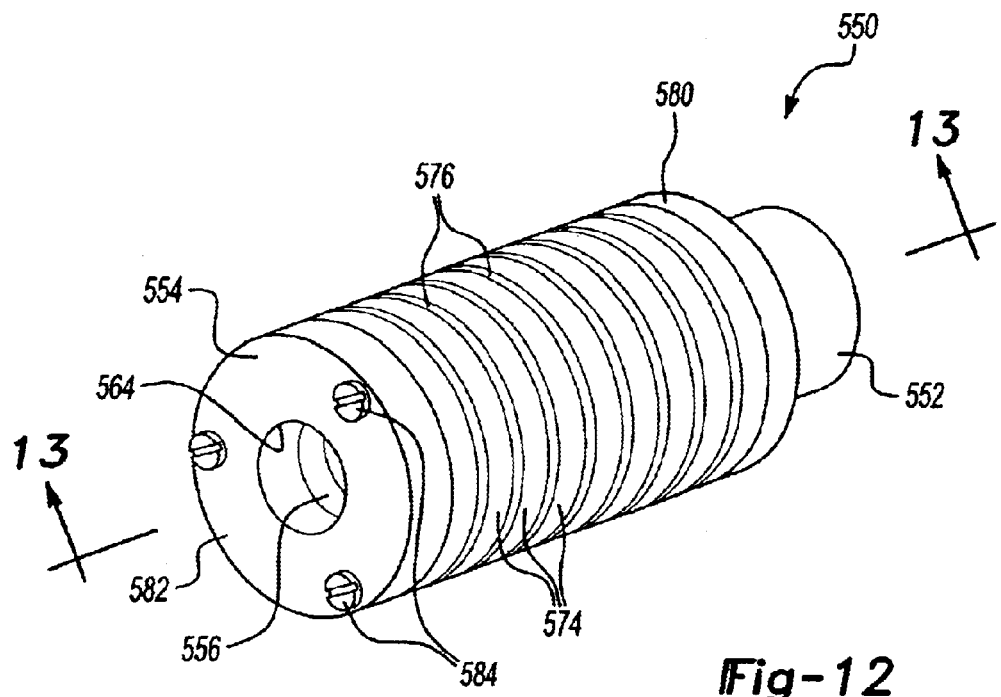
FIG. 12 illustrates a perspective view of an exemplary tool for microcentrifugation of materials according to an aspect of the present invention.
Figure 13:
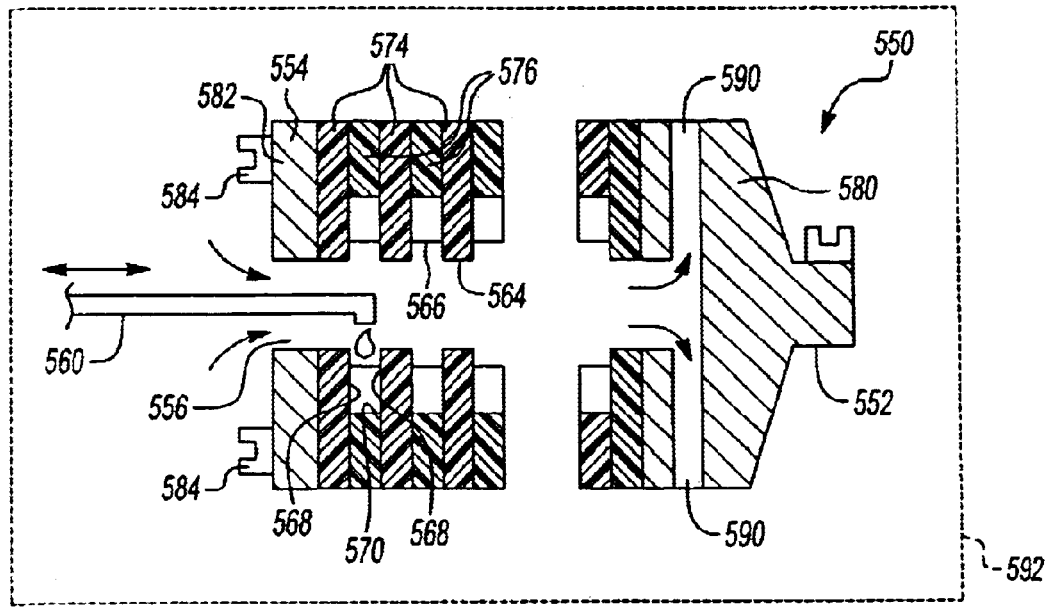
FIG. 13 illustrates a sectional view of the exemplary tool of FIG. 12 taken along line 13—13.

Turning to FIGS. 12 and 13, there is shown yet another approach to preparing samples (whether blends or not) in accordance with the present invention, by the use of an illustrative microcentrifugation technique. This approach has the advantage that a plurality of material samples may be formed at the same time and the material samples will be generally near net or final shape for the desired test to be performed. Generally, this technique is useful primarily for sample preparation. However, some mixing may result from its use.

More specifically, a tool 550 having a longitudinal axis is provided with a first end 552 and a second end 554. The first end has suitable fittings for permitting it to be attached to a rotor of a suitable motor for rotation about the longitudinal axis. The second end optionally has an opening 556 defined therein for permitting access to the interior of the tool and optionally the flow of fluids therethrough (e.g., for drawing or removing solvents or gasses along the axis). In one embodiment, the opening extends from the second end toward the first end, and more preferably extends substantially the entire length of the tool within which material samples are to be prepared. The opening is defined for allowing fluid flow therethrough, and preferably over substantially the entire length of the tool within which material samples are to be prepared. Advantageously, it is also configured for permitting passage of a dispenser 560 (e.g., associated with a robot arm) therethrough, for enabling introduction of fluids to the interior of the tool.

The tool has an interior wall surface 564 configured for defining one or a plurality of axial separated radial wells 566. In the embodiment shown for example, the wells have generally orthogonally disposed walls 568 relative to an inner wall 570. However, other topographies are also possible. For making the tool in accordance with FIGS. 12 and 13, it is therefore possible to stack a plurality of first washers 574 of different inner diameter relative to a plurality if interspersed second washers 576. Additional washers of other diameters or thicknesses (i.e., the longitudinal dimension) may also be used. In one preferred embodiment, the washers are Teflon spacers. Examples of preferred thicknesses range from about 0.1 mm to about 10 cm and more preferably about 1 to about 10 mm, with inner diameters ranging from about 1 mm to about 50 mm, and more preferably about 5 mm to about 25 mm. The ratio of thickness to diameter may vary as well, e.g., from about 0.1:50 to about 100:1; and more preferably from about 1:25 to about 2:1. Other ratios may also be employed within the scope of the invention.

The first and second washers are assembled with a suitable holder. For example, a first end plate 580 is connected with a second end plate 582, such as with bars, rods, wires, threaded fastener 584 or the like. Upon tightening the fasteners, the washers are brought together, for instance, in contact with each other.

The washers may be coated or otherwise surface treated. An intermediate layer, such as a paper, foil, film, a grease, oil or the like may also be employed between washers for facilitating washer separation and material sample removal.

In accordance with the above, polymer in a fluid state (e.g., molten, dissolved or the like) is introduced into the opening 556 and dispensed into the respective radial wells 566. The tool is rotated about its longitudinal axis for effectively centrifuging the material in the wells, for forming samples and for possibly having the effect of mixing the materials therein. Devolatilization may occur through the opening 556 or through optional radial passageways 590. Resulting material samples are generally ring-shaped, but can be varied by varying the axis of tool rotation, the topography of the tool interior, or the like.

It will be appreciated that modifications to the above may also be made to render the tool suitable for orbital or other forms of rotation.

Optionally, the tool 550 is enveloped partially or in whole in a suitable thermal jacket 592 (schematically shown with dashed lines) or other structure for insulating, heating or cooling the tool 550. The tool 550 may also be enclosed in a chamber in which the pressure can be reduced by applying a vacuum, such as for speeding the removal of solvents. The thermal jacket may be used for any of a number of functions, such as controlling trigger temperatures for crosslinking.

Molding

Another approach to the preparation of material samples involves the molding of materials, whether blended or not. As with other processes disclosed elsewhere herein, this process can be employed with dissolved polymers, molten polymers, or a combination thereof.

In one embodiment, a substrate with wells is provided. The materials, either alone, or mixed together in an upstream mixing, are dispensed in a fluid state to the wells. Upon cooling, evaporation or otherwise solidifying the mixture of materials, the resulting blend assumes generally the form of the wells, the walls of the wells having effectively functioned as a mold wall.

The substrate of this embodiment may have a fixed bottom surface, or no bottom surface. In the event of the latter, during molding, a separate base surface is provided onto which the fluidic material can rest upon dispensing.

Optionally a top plate may be provided for applying pressure to or otherwise confining the material as it solidifies. Though the top plate may be relatively smooth or flat, advantageously it may contain one or more projections for mating disposition relative to the wells. The projections effectively function as plungers for compressing the material in the wells. The top plate and the underlying substrates may be suitably attached to each other, e.g., by fastening with a fastener or some other attachment for permitting clamping.

Figure 14:
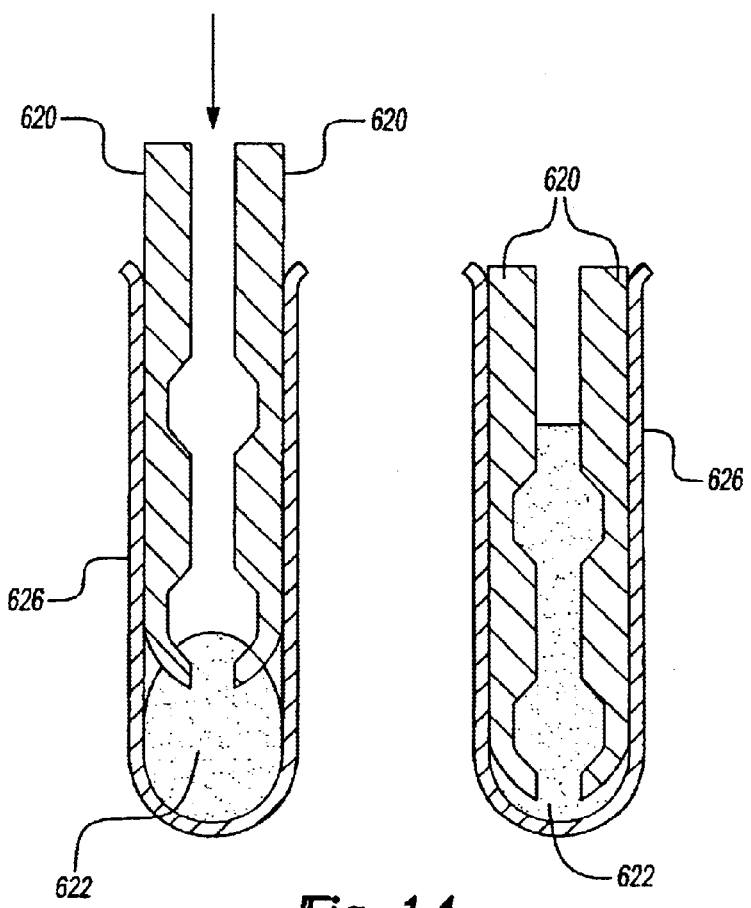
FIG. 14 illustrates an exemplary apparatus for molding materials according to an aspect of the present invention.

Turning now to FIG. 14, another molding approach is illustrated. In this example, a mold is defined by at least two opposing mold portions 620 (optionally with embedded heaters, coolers and temperature controller), having the desired article configuration defined therein. Preferably, the mold portions are placed joined together to define an inlet 622 for receiving the material to be molded. Optionally, the mold portions are placed into a further receptacle, such as a vial 626, (e.g., a vial employed in a polymerization process, such as that of U.S. application Ser. No 09/826,606, incorporated by reference) and material to be molded is introduced within the mold cavity.

One particularly preferred approach, illustrated in FIG. 14 involves placement of the mold portions in contact with a plastic material (e.g., one that has been blended already, a mixture of materials for blending, or an unblended material). The plastic material is heated to a temperature greater than its melting point. The fluid material then enters the mold cavity. Upon cooling it can be removed from the mold. In this approach, the mold portions may themselves be heated, the entire system may be subjected to heat, or a combination thereof. Further, a pressure may be applied for causing the mold to itself enter the mass of molten plastic material thereby introducing material into the mold, the weight of the mold itself may cause such entry, an external force (e.g., a plunger or a suction) may be applied for causing material to enter the mold, or a combination thereof.

Molding may be accomplished using any other art-disclosed molding technique. Additionally, bulk shapes can be molded using art-disclosed techniques and then machined or otherwise processed to the final desired shape.

Substrates

Libraries of samples may be, but are not necessarily, supported by one or more substrates. Depending upon the purpose of the samples, it may be advantageous in certain instances to provide samples without one or more common substrate while, in other instances, it may be advantageous to support the samples upon one or more common substrates. When used, the substrate onto which the ingredients are dispensed may be any suitable substrate. Substrates suitable for the present invention may include a plurality of wells. The wells may be formed in variety of shapes and configurations. Wells may generally be, without limitation, square, rectangular, cylindrical, straight, angular, curved, deep, of any depth or any other shape or size. Wells may be defined by walls of a member or substrate into which the wells extend. Alternatively, a member or substrate may have raised portions to define wells. Moreover, wells may be defined within a single continuous portion of a substrate or the substrate may comprise more than one portion or member that come together as an assembly to form the wells. A substrate may also be comprised of vials, glass tubes or other containers that have wells and can be supported by a vial rack or other suitable support member. In one preferred embodiment, the substrate is a plural well microtiter plate (e.g., having 96 wells, with less than about 5 ml/well volume).

In one approach, the substrates may be suitable for supporting a sample or library of samples provided or formed by spray drying. For example, components of polymer blends (e.g., polymers, solvents and the like) may be emitted through one or more spray-drying nozzles and optionally through a physical mask and onto a substrate. Components may be emitted in solid, liquid and/or gas form. Optionally, the samples formed by spraying may be further processed by drying or annealing in a vacuum furnace and may be further shaped by pressing or trimming.

According to one aspect, one or more substrates may be formed with a member having through-holes extending through the member. Typically the through-holes will have at least two ends each with an opening. The through-holes may be defined by walls of the member and the walls may be configured to form, cast or mold samples into a desired shape or configuration. Additionally, a removable backing member may be provided that is suitable for covering one of the openings of the through-holes such that the walls of the through-holes together with the backing can form wells.

Referring to FIGS. 17(a)–19(b) (where like reference numerals refer to like parts), for instance, there are illustrated embodiments of substrates suitable for receiving components for forming material sample libraries. A substrate 800, 802, 804 includes a first member 810, which is a block, but which, may be formed in any configuration such as a cylinder, a cone or the like. The member 810 includes a plurality (e.g., 96) of through-holes 812 extending through the member 810. The through-holes 812 shown are generally cylindrical although they may be in a variety of shapes or configurations. Preferably, the through-holes 812 will have at least two ends each with an opening defined in one or more surfaces of the member 810. The member 810 may be formed of a variety of materials such as polytetrafluoroethylene (PTFE) (e.g., TEFLON®) or any other suitable materials.

The substrate 800, 802, 804 may also include a backing member such as a plate 820 that may engage (e.g., abuttingly contact) the member 810. The plate 820 may be configured to engage the member 810 so as to cover an opening of each of the through-holes 812 of the member 810 thereby forming the through-holes 812 into wells. The plate 820 may be attached to the member 810 with fasteners (not shown) such as screws, clamps, nut and bolt assemblies and the like or with adhesives or any other attachment mechanism. Preferably, the attachment mechanism is releasable such that the plate 820 may be removed from the member 810 as needed or desired. Additionally, the plate 820 may be formed of a variety of materials such as a polyimide (e.g., KAPTON®) or any other suitable materials or may be coated with a film of polyimide or another suitable material.

Figure 17A:
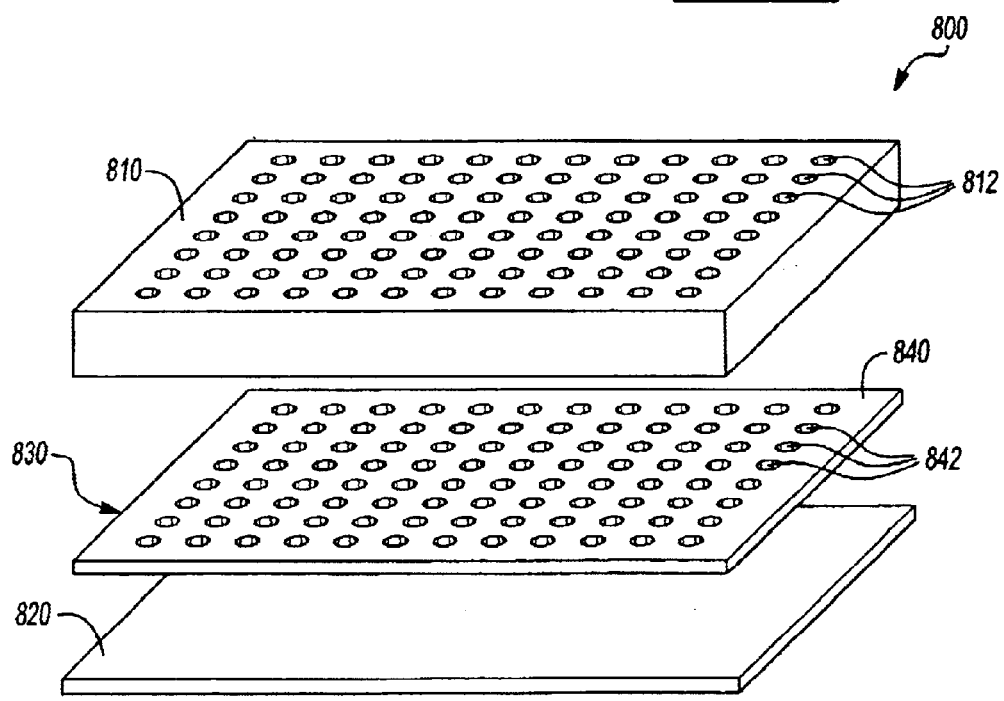
FIG. 17(a) illustrates an exploded perspective view of an exemplary substrate in accordance with an aspect of the present invention.
Figure 17B:
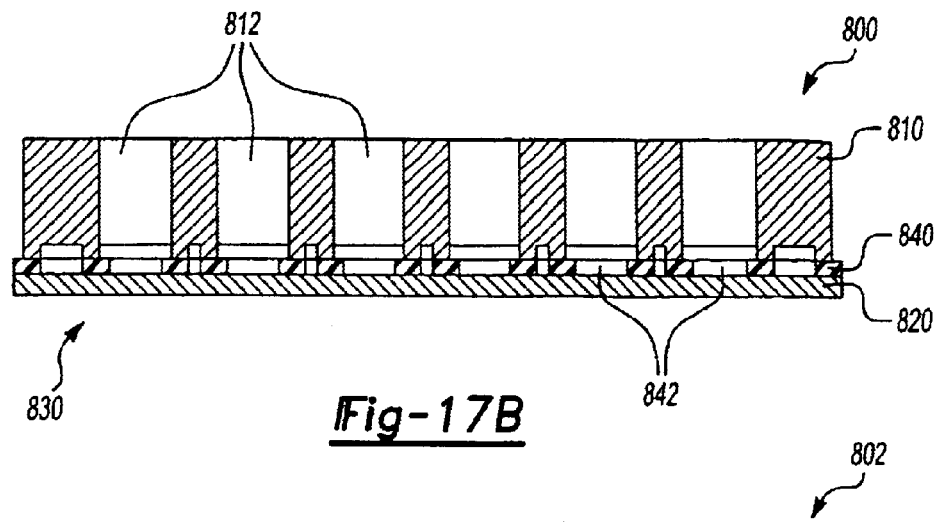
FIG. 17(b) illustrates a sectional view of the substrate of FIG. 17(a) in an assembled condition in accordance with an aspect of the present invention.
Figure 18A:
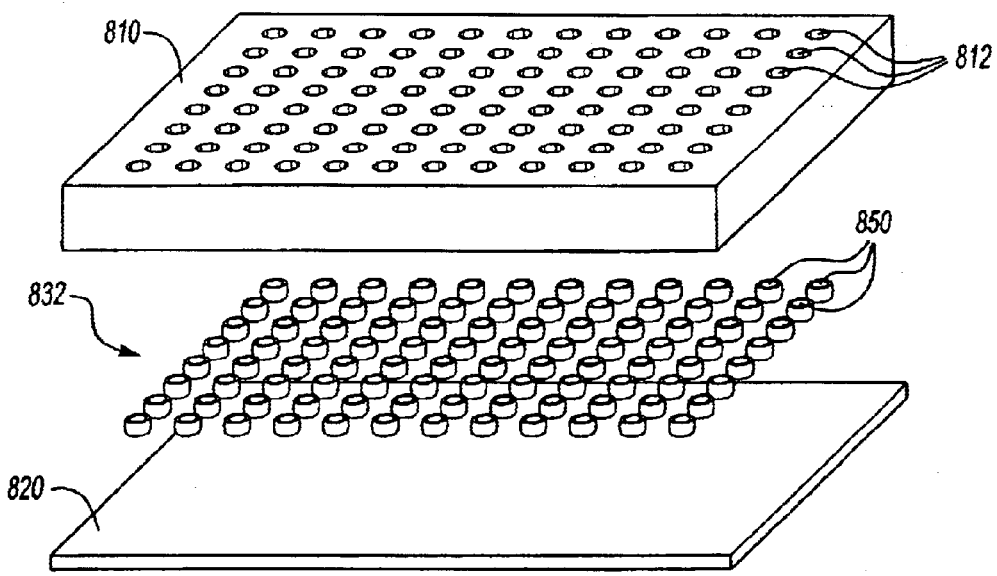
FIG. 18(a) illustrates an exploded perspective view of an exemplary substrate in accordance with an aspect of the present invention.
Figure 18B:
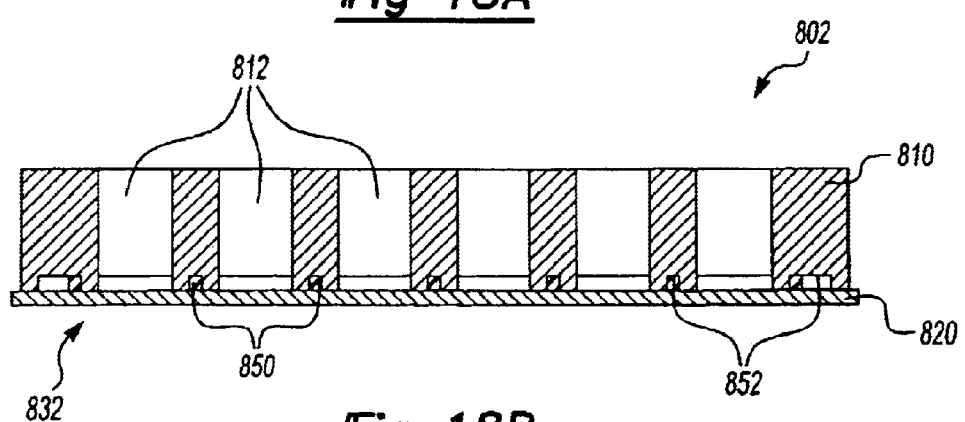
FIG. 18(b) illustrates a sectional view of the substrate of FIG. 18(a) in an assembled condition in accordance with an aspect of the present invention.
Figure 19A:
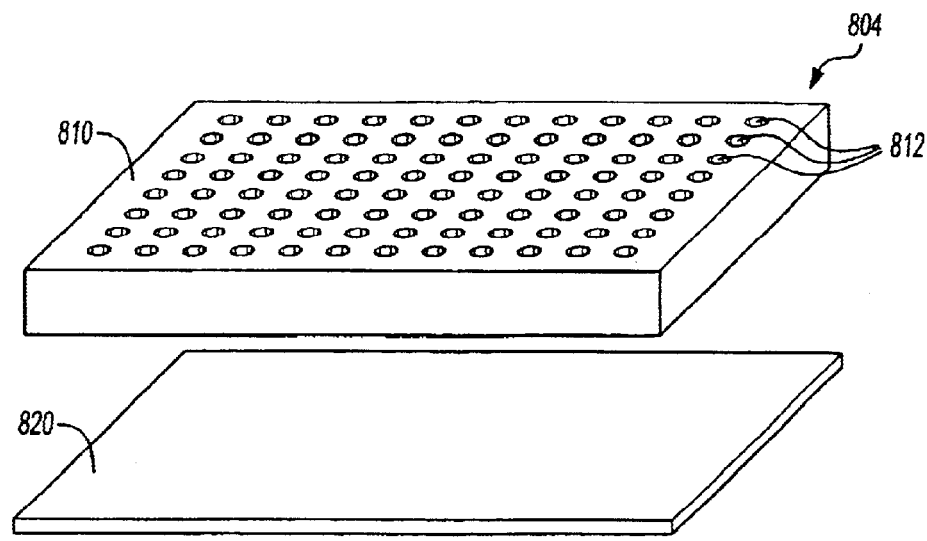
FIG. 19(a) illustrates an exploded perspective view of an exemplary substrate in accordance with an aspect of the present invention.
Figure 19B:
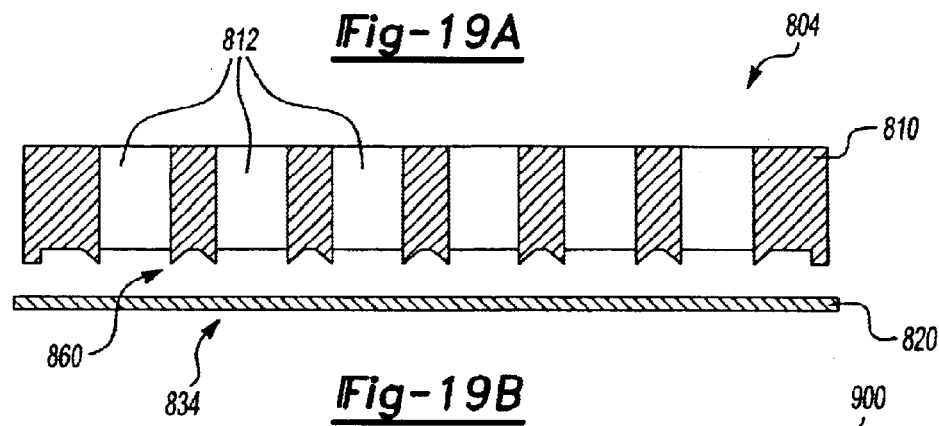
FIG. 19(b) illustrates a sectional view of the substrate of FIG. 19(a) in an assembled condition in accordance with an aspect of the present invention.

Each of the substrates 810, 812, 814 also include a system 830, 832, 834 for forming a substantially fluid or liquid tight seal between the through-holes 812 or wells of the substrates 810, 812, 814. In FIGS. 17(a) and 17(b), the system 830 is comprised of gasket 840 (e.g., formed of an elastomer) that includes through-holes 842 corresponding to the through-holes 812 of the member 810 such that the through-holes 842 of the gasket 840 align with the through-holes 812 of the member 810 when the gasket 840 is sandwiched between the member 810 and the plate 820. In FIGS. 18(a) and 18(b), the system 832 is comprised of a plurality (e.g., 96) of O-rings 850 (e.g., formed of an elastomer or other plastic) that are configured to at least partially reside in channels 852 that extend about openings of the through-holes 812 of the member 810 when the O-rings 850 are sandwiched between the member 810 and the plate 820. In FIGS. 19(a) and 19(b), the system 834 is comprised of pointed edges 860 surrounding an opening of the through-holes 812 of the member 810 wherein the edges 860 are configured to contact the plate 820 when the plate 820 is attached to the member 810 thereby forming a seal about one of the openings of the through-holes 812 of the member 810.

Preferably, the member 810, the plate 820 and the systems 830, 832, 834 are formed of materials that are substantially inert with respect to any components or samples that contact those portion of the substrates 800, 802, 804.

It shall be appreciated that, although the above substrates 800, 802, 804, includes generally cylindrical through-holes 812 for forming substrates with generally cylindrical wells, substrates may be formed with wells of most any configuration. Preferably, each of the wells is or includes a cast portion for assisting in the formation and/or solidification of solid materials. A cast portion, as used herein, refers to any open space defined by one or more walls wherein the space is suitable for receiving a material sample and the one or more walls are suitable for supporting the material sample as the sample is solidified to a predetermined configuration that is at least partially defined by the one or more walls. Cast portions for the substrates 800, 802, 804 of FIGS. 17(a)–19(b) may be any portion of the wells of those substrates 800, 802, 804 that receive material samples and those portion may form generally cylindrical samples since the wells are almost entirely cylindrical. It is contemplated, however, that cast portions, wells or both may be formed in a variety of configurations and shapes and cast portion. Examples of potential shapes of cast portions or wells include trapezoids, blocks, rings, cubes, cylinders, spheres, hemispheres, polyhedrons, prisms, pyramids, dog bone shaped or any other conceivable shape. Cast portions and there uses are further discussed below in sections titled "Material Sample Solidification" and "Materials Characterization".

Material Sample Solidification

The present invention contemplates the use of various suitable techniques for solidifying at least partially fluidic material samples that may be supported by substrates. Generally, samples may be solidified by evaporating solvents from the samples, artificially cooling or allowing natural cooling of samples, drying samples, chemically or otherwise reacting samples or a combination thereof. Alternatively, other solidification techniques may be used as well.

To assist is solidification, the samples may be exposed to various stimuli such as force, pressure, vacuum conditions, elevated temperatures (e.g., heating), lowered temperatures (e.g., cooling) and the like. Force, pressure or vacuum conditions may be applied by increasing gas pressure about the samples to above atmospheric pressure or by lowering gas pressure about the samples to below atmospheric pressure. Alternatively, force or pressure may be applied to the samples by rotating the samples with a rotation apparatus (e.g. a centrifuge) or other apparatus to provide centrifugal or centripedal force or pressure to the samples. According to one aspect of the invention, though contact pressure might be employed, preferably pressure is applied to at least one surface of a sample without contacting that surface with another solid structure. For example, this might be accomplished by applying gas pressure to the surface, applying centrifugal force or pressure to the surface and the like. Simultaneously therewith, it is possible that heat may be applied to the sample for causing evaporation of the solvent, or rendering the sample less viscous. Assuming that surface bubbling or foaming is undesired in the final sample, preferably the non-contact pressure source is sufficiently controlled for bursting any bubbles that may form at or near the surface and for rendering the surface substantially smooth. This may be done for instance by the pressure choice for the non-contact pressure, the duration of any pressure pulse employed, the frequency of any pressure pulse employed, the temperature of any gas directed at the surface, or in another suitable manner.

Temperatures of samples may be controlled according to any of a variety of methods. As an example, gas (e.g., air) surrounding a substrate of samples may be elevated or lowered to adjust temperature of the sample. As another example, the temperature of a substrate or an individual region thereof may be controlled for affecting the temperature of the samples supported by that substrate. Exemplary heating devices for raising or lowering the temperatures of samples include heating elements, infrared (IR) lamps, thermoelectric elements, refrigeration systems and the like.

Figure 20:
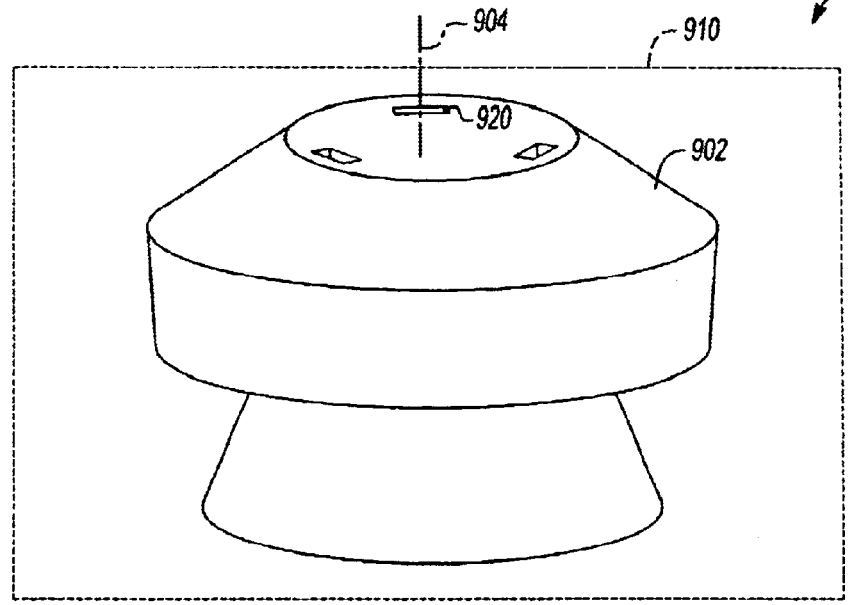
FIG. 20 illustrates a perspective view of an exemplary system for assisting in solidifying material samples in accordance with an aspect of the present invention.

With reference to FIG. 20, there is illustrated an exemplary system 900 for solidifying libraries of material samples. The system 900 includes a centrifuge 902 that rotates about a central axis 904. The system may be enclosed in a chamber 910 as indicated by the dashed line about the centrifuge 902. The centrifuge 902 may be partially, substantially or entirely enclosed within the chamber 910.

It is contemplated that the system 900 may have the ability to elevate or lower the temperature inside the chamber 910. Moreover, the system 900 may have the ability to form a partial of full vacuum within the chamber 910. Thus, the system 900 may have the ability to expose samples placed within the chamber 910 to higher or lower temperatures and to vacuum conditions.

An exemplary chamber/centrifuge system is the HT-12 Series II evacuated centrifuge from Gene-Vac Technologies, Great Britain. Although systems having a centrifuge within a chamber may be known, the system 900 of FIG. 20 has been adapted to process one or more entire libraries of samples. More specifically, the system 900 may include one, two, three, four or more locations 920 suitable for receiving several samples or libraries of samples. Preferably, libraries of samples are supported upon one or more substrates and each of the substrates can be suitably secured at the one or more locations 920. The locations 920 may be comprised of a cavity or recess formed in the centrifuge 902 or such cavity or recess may be formed within a member that is attached to the centrifuge 902. Moreover, the cavity or recess may be shaped to matingly receive one or more substrates. Additionally, fasteners (not shown) such as clamps, bolts, hook and loop fasteners or the like may be used to assist in securing substrates at the locations 920.

In operation, the system 900 may be used to expose the samples to various stimuli to assist in the solidification of the samples. In particular, one or more substrates supporting libraries of at least partially fluidic (e.g., liquid) material samples may be positioned, secured or both upon the centrifuge 902. Thereafter, the centrifuge 902 may be rotated at a desired rate to assist in the solidification of the samples to a desired configuration. Preferably, the samples solidify upon a plate or other member such as the backing plates 820 of the substrates 800, 802, 804 shown in FIGS. 17(a)–19(b) thus allowing the plates 820 and samples to be removed from the remaining portions of the substrates 800, 802, 804.

To assist in removing the samples without disturbing the shape or configuration of the samples, a suitable mold release agent may be employed. Alternatively, where there are known to be differences in the thermal expansion coefficients of the substrate relative to the sample, heating or cooling of the sample, substrate or both may be done. For example, the substrate, sample or both may be exposed to a fluid such as liquid nitrogen for lowering the temperature of the samples prior to removal.

The rotation of the centrifuge 902 may assist the formation of the samples in a variety of ways. For example, and without limitation, the rotation of the centrifuge 902 may apply a centrifugal force or pressure to the samples as any solvent that may be in the samples is evaporated. Such pressure can assist the samples in resisting any foaming during evaporation of the solvents thereby assisting in solidifying the samples to have a substantially uniform internal consistency. Additionally, such pressure may be applied while leaving one exposed surface of each sample for allowing solvent to evaporate away while still allowing that exposed surface to be relatively smooth when the sample solidifies. Moreover, applying force or pressure with a rotating apparatus that rotates at a consistent speed can assist in providing a consistent stress/strain history for each of the samples of the substrate as they solidify. Thus, comparisons between the samples in later materials testing situations may be more meaningful since any differences detected between the samples are less likely to be due to differences caused by the solidification of the samples and are more likely to be due to differences in characteristics of the samples that are being tested.

The system 900 may also be used to expose the sample to other stimuli such as vacuum conditions and elevated temperatures for evaporating solvents. The system may also expose the samples to lowered temperatures for bringing the temperatures of samples below their melting points for solidifying the samples regardless of whether the samples include solvents. As an example, the chamber 910 may be closed to isolate the material samples from the environment surrounding the chamber 910. Then, before, during or after rotation of the samples, partial vacuum conditions and elevated or lowered temperatures may be induced within the chamber 910 to expose the samples of the libraries to such stimuli.

Advantageously, a rotatable apparatus (e.g., a centrifuge) of the invention may be configured to apply pressure or force to a liquid or fluid sample to assist in positioning the sample in the previously discussed cast portions of the wells of the substrates. With reference to FIG. 20, substrates may be adjustably positioned at a greater or lesser angle with respect to the central axis 904 of the centrifuge 902 such that the material samples can solidify within the predetermined cast portions of the wells such that the cast portions assist in defining the samples into desired configurations. For example, a substrate such as the substrate 800 of FIGS. 17(a)–17(b) might be positioned upon the centrifuge at a predetermined angle with respect to the central axis 904 such that the centrifuge 902 may be rotated at a predetermined rate that results in the formation of material samples that are substantially cylindrical.

For material samples that solidify by evaporating solvents, it may be desirable to form the samples in stages. Depending upon the desired thickness of the samples, a portion of several samples may dispensing and solidified as described herein followed by dispensing and solidifying secondary portions of the samples until the samples are formed to a desired thickness.

Figure 21:
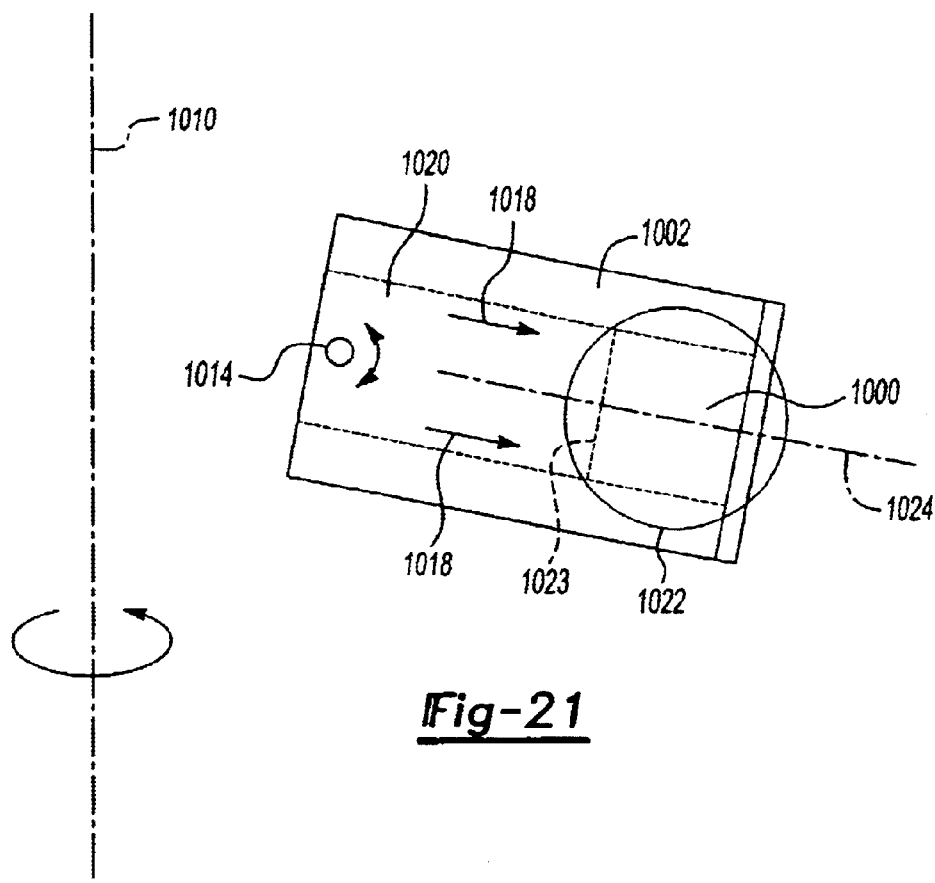
FIG. 21 illustrates a perspective view of another exemplary system for assisting in solidifying material samples in accordance with an aspect of the present invention.

In preferred embodiments, it is contemplated that individual samples or a substrate supporting a library of samples may be rotatable about two or more axes during solidification of the samples. Referring to FIG. 21, an exemplary sample 1000 of a library of samples is supported by a substrate 1002. The sample 1000 may be rotated about a central axis 1010 by a rotating apparatus (e.g., a centrifuge). Moreover, the substrate 1002 may be attached to the rotating apparatus with a pin or other fastener that allows rotation such that, as the sample is rotated about the central axis 1010, the substrate 1002 the sample 1000 or both may be allowed to rotate about a secondary axis 1014 generally perpendicular to the central axis 1010. Preferably, the secondary axis 1014 is located between the sample 1000 and the central axis 1010 as the sample is solidified.

During rotation of the sample 1000, centripedal force, centrifugal force, gravitational force or a combination thereof act on the sample 1000 to form a resultant force or pressure 1018 on the sample 1000 wherein the resultant force or pressure 1018 acts in a direction that is typically non-parallel or skew to the central axis 1010. Because the sample 1000, substrate 1002 or both are generally free to rotate about the secondary axis 1014, the sample 1000 tends to flow into a cast portion 1022 of a well 1020 such that an exposed surface 1023 of the sample 1000 forms a plane, and the normal to this plane is generally given the resultant force 1018 acting on the sample 1000. Moreover, the sample 1000 is allowed to solidify as defined by the cast portion 1022 and, if desired, the cast portion 1022 may be configured for forming a substantially symmetrical sample 1000 (e.g., cylindrical or symmetrical about a central axis 1024).

It is contemplated that providing libraries of at least partially fluidic samples may include initially providing the samples in solid form followed by melting the samples and then resolidifying the samples. For example, and with reference to FIG. 20, samples may be provided in wells of substrates as solids and the substrates may be secured upon the centrifuge 902. The temperature within the chamber 910 may be elevated to liquefy the samples before or during the rotation of the centrifuge. As the samples liquify, they may assume the predetermined configuration of the cast portions of the wells of the substrate. Then, the temperature within the chamber 910 may be lowered to solidify the samples into the predetermined configuration.

Figure 22:
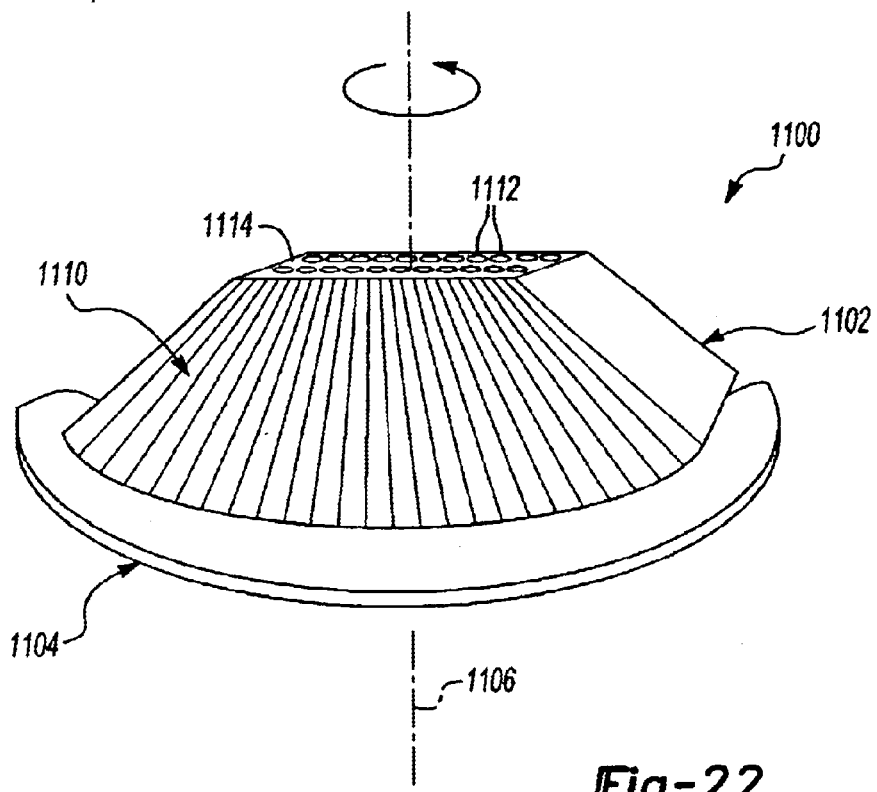
FIG. 22 illustrates a perspective view of yet another exemplary system for assisting in solidifying material samples in accordance with an aspect of the present invention.

In other alternative embodiments, the substrate itself may be configured as trapezoidal or conical in shape to correspond to the spinning of the centrifuge. Referring to FIG. 22, there is illustrated a substrate 1100 having a generally trapezoidal member 1102 positioned on a generally curved removable backing plate 1104 (e.g., made at least partially of a plastic, such as a polyimide). The trapezoidal member 1102 (e.g., made at least partially of PTFE) includes a plurality of through-holes 1110 extending from openings 1112 in a generally flat surface 1114 of the member 1102 to openings (not shown) in a curved surface (not shown) of the member 1102 wherein the through-holes form wells when the backing plate 1104 covers the openings in the bottom of the cone-shaped member 1102. Preferably, the backing plate 1104 is curved to correspond to and fit flush against the curved surface of the trapezoidal member 1102.

In operation, material samples or components of material samples may be dispensed through the openings 1112 in the surface 1114 of the cone-shaped member 1102. Thereafter, the substrate 1100 may be attached to and rotated by a centrifuge system to solidify the samples substantially as described below. Preferably, the samples are formed or solidified upon the plate 1104 such that the plate 1104 and the samples may be removed from the trapezoidal member 1102. In a highly preferred embodiment, the through-holes 1110 of the trapezoidal member 1102 are disposed at angles relative to the plate 1104 such that the force (e.g., the combination of centrifugal and gravitational forces) placed on the samples during rotation is normal to a surface of the plate 1104 on which the samples solidify. In still another highly preferred embodiment, the corresponding curvature of the surface of the trapezoidal member 1102 and the curvature of the backing plate 1104 are also configured relative to the axis of the centrifuge such that the force (e.g., the combination of centrifugal and gravitational forces) placed on the samples during rotation is normal to a surface of the plate 1104 on which the samples solidify.

In still other alternative embodiments, material samples may be extruded. For example, a rotatable system may include holes, which act as dies. Accordingly, samples may be positioned such that the centrifugal force of the rotatable system urges the material samples into or through the dies in a partially fluidic state (e.g., as polymer melts or viscoelastic polymers) and, in turn, the samples are shaped into a desired predetermined configuration.

Figure 23:
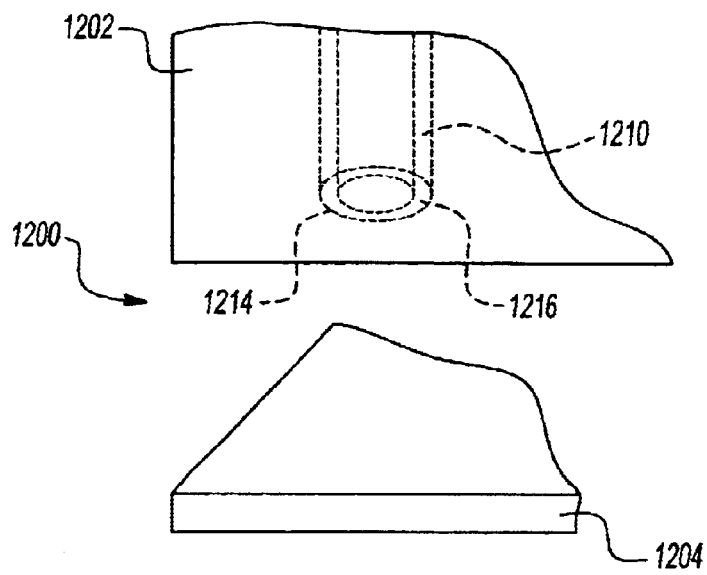
FIG. 23 illustrates a partially cut-away exploded perspective view of an exemplary substrate in accordance with an aspect of the present invention.
Figure 23A:
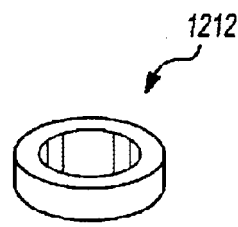
FIG. 23(a) illustrates an exemplary material sample formed using the substrate of FIG. 23 according to an aspect of the present invention.

Depending on the intended purpose (e.g., material characterization or testing) of the materials, cast portions of wells in substrates may form samples according to a variety of configurations or shapes. With reference to FIG. 23, there is illustrated a substrate 1200 with a block 1202 and a backing plate 1204. The block 1202 includes a through-hole 1210 that is generally annular in shape for forming a well with the backing plate 1204 when the backing plate 1204 is used to cover an opening 1214 at an end of the through-hole 610. The well includes a casting portion 1216 appropriate for casting a ring or annular shaped sample 1212 as shown in FIG. 23(*a*). In the embodiment of FIG. 23, the casting portion 616 may extend along the through-hole 1210 as far as needed or desired depending upon the desired thickness of the sample 1212.

Figure 24:
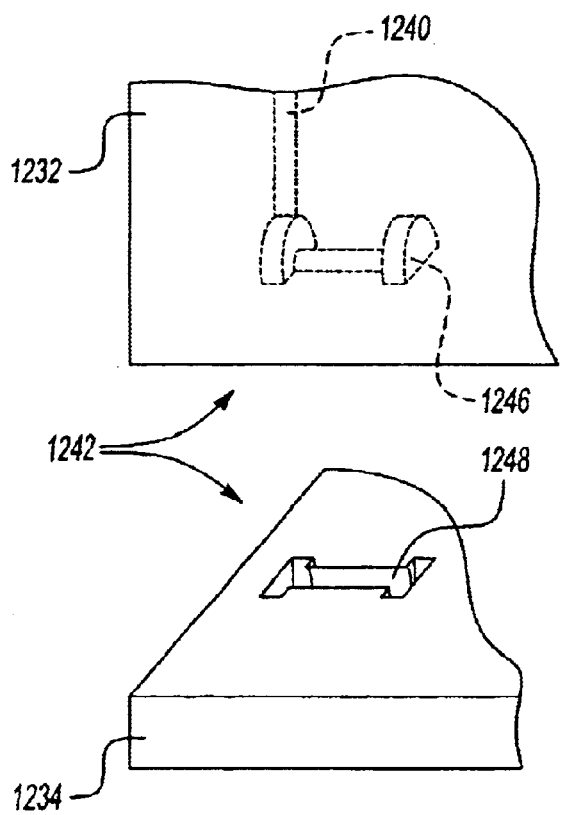
FIG. 24 illustrates a partially cut-away exploded perspective view of an exemplary substrate in accordance with an aspect of the present invention.
Figure 24A:
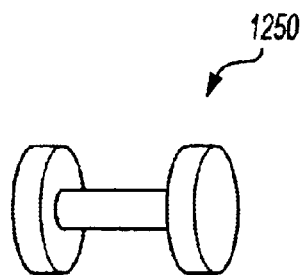
FIG. 24(a) illustrates an exemplary material sample formed using the substrate of FIG. 24 according to an aspect of the present invention.

With reference to FIG. 24, there is illustrated another substrate 1230 with a block 1232 and a backing plate 1234. The block 1232 includes a through-hole 1240 that opens into a mold portion 1242. The mold portion 1242 is comprised of two cavities 1246, 1248, one that extends into the block 1232 and one that extends into the backing plate 1234. When the plate 1234 is secured to the block 1232, the cavities 1246, 1248 cooperatively form the mold portion 1242 into a dumbbell shape (i.e., with a thinner portion between two thicker portions) for forming dumbbell shaped sample 1250 as shown in FIG. 24(*a*).

It should be appreciated from the foregoing that material samples may be formed or solidified in any desired shape by forming a cast portion defined by walls that correspond to the desired shape. Thus, it is possible according to the present invention to form material samples as trapezoids, blocks, rings, cubes, cylinders, spheres, hemispheres, polyhedrons, prisms, pyramids, dog bone shaped or other geometric or irregular shapes. Moreover, any number of wells or cast portions may be formed in a substrate for producing a desired number of samples.

Film Preparation

Material samples may also be provided according to the present invention by dispensing material samples onto a flexible substrate (e.g., a webbing) to form films. Accordingly, a suitable flexible film is provided for receiving and supporting a plurality of samples. Preferably the plurality of material samples is provided in a fluidic state (e.g., as a liquid). Thereafter, the plurality of samples is dispensed upon the webbing and is solidified to form films.

The samples may be dispensed to the webbing in a variety of manners. Samples may be dripped, squirted, coated, extruded or the like onto the webbing. According to one embodiment, the samples are dripped from a syringe, capillary or like dispenser using an automatic system (e.g., a robot or like system) onto various regions of the webbing. For dispensing onto various regions, the dispenser may be moved relative to the webbing, the webbing may be moved relative to the dispenser or a combination thereof. The samples that are dispensed may be physically separate or a flow of sample materials may be established wherein a sample variable (e.g., composition, density or the like) of the flow varies with respect to time such that a substantially continuous film of varying samples is formed on the webbing.

If needed, the samples may be formed or shaped to form films after they have been dispensed upon the webbing. For example various tools such as blades, edged tools, casting tools and the like may be used to shape samples after they are dispensed. Preferably, any tools used for shaping of samples are clean prior to contacting the samples. Accordingly, a tool may be washed after it shapes each sample, a different tool may be used for each sample or a tool may include multiple shaping portions, each for contacting a separate sample.

Solidification of the samples may be accomplished according to various techniques such as precipitation, temperature change, solvent evaporation, humidity, immersion in a non-solvent, drying and the like. Once formed, the films of material samples may remain on the webbing for further testing or screening or the films may be removed from the webbing.

Figure 25A:
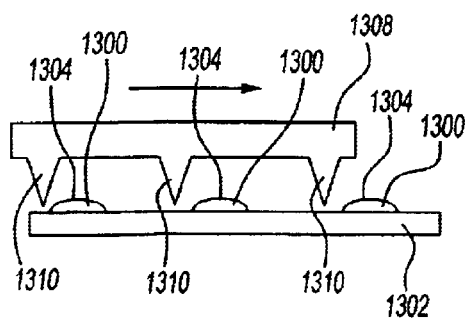
FIGS. 25(a) and 25(b) illustrate exemplary material samples being formed into films upon a substrate according to an aspect of the present invention.
Figure 25B:
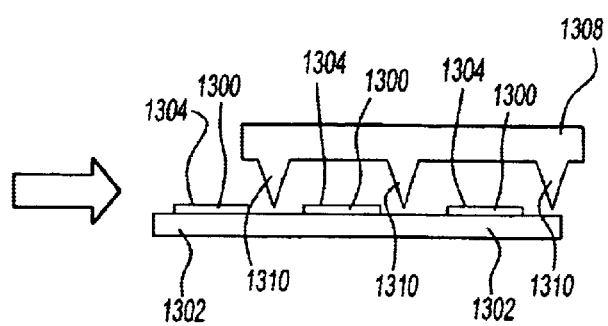

Referring to FIGS. 25(*a*) and 25(*b*), there is illustrated a plurality of substantially liquid material samples 1300, which have been dispensed upon a webbing 1302. After dispensing, as shown in FIG. 25(*a*), the samples 1300 have generally curved upper surfaces 1304. Therefore, a tool 1308 having multiple edged protrusions 1310 is translated relative to the webbing 1302 and the samples 1300 such that an edge of each of the edged protrusions 1310 contacts and flattens the upper surfaces 1304 of the samples 1300 thereby forming films.

Figure 26:
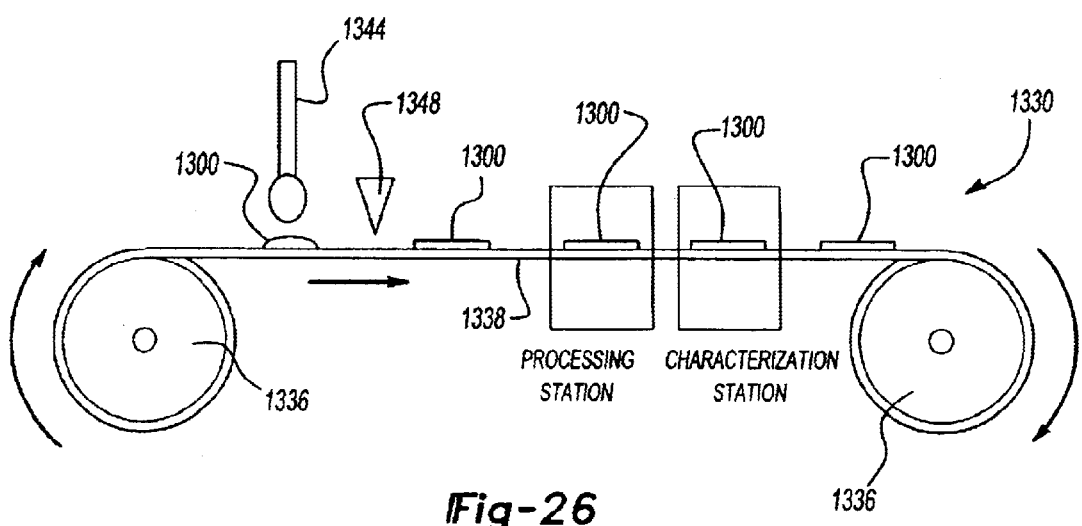
FIG. 26 illustrates exemplary material samples being formed into films upon a substrate according to an aspect of the present invention.

Referring to FIG. 26, there is illustrated a system 1330 for forming material samples 1300 into films followed by processing and characterizing the material samples 1300. The system 1330 includes a pair of spaced apart rollers 1336 and a webbing 1338 wherein the webbing 1338 is translatable between the rollers 1336 by rolling the webbing 1338 onto one of the rollers 1336 while simultaneously rolling the webbing 1338 off the other roller 1336. As the webbing 1338 translates between the rollers 1336, a capillary tube 1344 dispenses the material samples 1300 onto the webbing 1338. Thereafter, the webbing 1338 translates the samples 1300 past an edged tool 1348, which flattens the samples 1300 into films. As the webbing 1338 continues to translate, the material samples 1300 may be passed through a processing station, a characterization station or both. In the processing station, the sample materials 1300 may be processed according to any variety of steps such as shaping, coating, curing and the like. According to one preferred embodiment, the sample materials 1300 are solidified in the processing station according to one of the techniques mentioned above. In the characterization station, the samples 1300 may be tested or screened for any number of properties. Such characterization techniques are further described below.

Without limitation, samples of various different commercially useful products may be formed as films and characterized according to the present invention. Examples include membranes, paints, various coatings, adhesives and the like.

Materials Characterization

For materials characterization, the samples may be formed in a variety of sizes and weights. For example, samples may have thicknesses as low as about 0.1 micron to about 25 mm. Moreover, exemplary ranges of weights for samples include ranges of about 1 microgram to about 0.5 kilogram or about 1 mg to about 100 mg or about 10 mg to about 80 mg.

Materials in accordance with the present invention can be analyzed for any of a number of its characteristics, including for instance chemical composition, morphology, physical property, decomposition, turbidity or other property of interest.

The libraries of material in accordance with the present invention lend themselves to any of a number of art-disclosed characterization techniques including but not limited to those employing beam radiation analysis, such as x-ray diffraction, high-throughput x-ray scattering, scattering from experimental systems, viscometry, failure or strength testing, adhesion testing, birefrigerance, rheo-optics, electron radiation, neutron radiation, sychotron radiation, or the like, infrared techniques (e.g., FTIR, IR detection or otherwise), thermal analysis techniques (such as differential scanning calorimetry, differential thermal analysis or the like), chromatographic techniques, resonance, spectroscopy, light scatter, spectrometry, microscopy, nuclear magnetic resonance, optical measurements, electro-chemical measurements. By way of example, X-ray diffraction (XRD) and X-ray fluorescence (XRF) can be used in combination to determine the material crystal structure and composition, respectively. Other suitable screens might be gleaned from commonly owned U.S. Pat. Nos. 5,776,359; 5,959,297; 6,013,199; 6,034,775; 6,087,181; 6,151,123; 6,157,449; 6,175,409; 6,182,499; 6,187,164; 6,225,487; 6,248,540; 6,256,226; 6,260,407 and U.S. application Ser. Nos. 60/300,792, filed Jun. 25, 2001; 09/680,154; 09/215,417; 09/667,119, 09/939,252, 09/580,024, and 60/314,842 (all of which are hereby incorporated by reference), as well as other commonly owned patent properties.

Samples may also be analyzed using art-disclosed techniques, for any of a number of different physical properties, such as tensile strength testing, impact strength testing, tear resistance testing, density testing, tack testing, viscoelastic modulus testing, rheology testing, viscosity testing, bulge testing, probe perturbation testing, flexure testing, optical testing, hardness testing, melt index testing, flow index testing, glass transition testing, melting point testing, flow impedance testing, surface roughness testing, light scattering property testing, die swell testing, order-disorder transition temperature testing, order-order transition temperature testing, fluid permeability testing, electrical property testing (e.g., dielectric constant) or other testing. Examples of such analytical techniques can be found in commonly owned U.S. Pat. No. 09/939,149, filed Aug. 24, 2001; U.S. Pat. No. 09/939,263, filed Aug. 24, 2001; U.S. Pat. No. 09/938,994, filed Aug. 24, 2001; U.S. Pat. No. 09/939,252, filed Aug. 24, 2001; U.S. Pat. No. 09/939,404, filed Aug. 24, 2001; U.S. Pat. No. 09/210,086, filed Dec. 11, 1998; U.S. Pat No. 09/954,449 filed Sep. 17, 2001 (all of which are hereby incorporated by reference). Other thermal or electrical properties may be analyzed such as conductivity, resistivity, or the like.

Samples may also be analyzed for response to cyclic loading, solvent/chemical resistance, weatherability, or other conditions for simulating actual operating conditions for a particular application. In yet another embodiment, materials are analyzed for their recycleability attributes.

It is also expected that characterization may also be employed using other art-disclosed techniques, including optical microscopy, scanning electron microscopy, or other microscopy techniques.

Thus, it can be seen how those of skill in this art can effectively utilize the methods of this invention for a combinatorial materials science research program.

Library Design Methodology

As can be appreciated from the above, the present invention provides an advantageous approach to the high throughput preparation and analysis of material samples. Though the preparation and analysis of individual test samples is contemplated within the scope of the present invention, in a particularly preferred embodiment, the present invention is used in the preparation and analysis of libraries of plural test samples for achieving high throughput rates.

In creating libraries in accordance with the present invention, it is frequently desirable to vary the compositions, stoichiometry or processing parameters of the starting materials, although it will be appreciated that a library of plural identical library members might be employed, wherein different of the library members are subjected to a different analysis (e.g., property test, screen or the like). It is also possible to vary the reaction environment conditions from region to region to create different materials or materials with different properties.

In the context of preparing and analyzing libraries of materials, it is contemplated that one or a combination of parameters can be varied within a library selected from composition, concentration, addition sequence, addition time, addition rate, temperature profile, temperature processing history, mixing type, mixing force, mixing rate, mixing history, shear strain, elongational strain, mixing torque, cure initiation time (e.g., chemical, thermal, physical), mixing environment, residence time distribution, molecular weight, compounding conditions, use of compatibilizing agents (e.g., for controlling hydrogen or ionic bonding, electron donor-acceptor complexes, or the like), radiation exposure, cyclical loading, solvent type, environmental exposure, or the like.

By way of illustration, with particular reference to the selection of the chemistry of a first and second different ingredient, it is possible that the first ingredient is constant across the substrate, but the second ingredient is varied region to region. Likewise it is possible to vary the first ingredient across the substrate, but maintain the second ingredient constant. Moreover, it is possible to vary both the first and second ingredients across the substrate.

Examples of ratios and techniques for forming a variety of libraries are illustrated in U.S. patent application Ser. No. 09/156,857 and Ser. No. 09/156,827 entitled "Formation of Combinatorial Arrays of Materials Using Solution-Based Methodologies," hereby incorporated by reference. Preferably a library is created having at least 4 different materials, more preferably at least 5, still more preferably at least 10. Amounts of different materials in excess of 10 are contemplated for a single library in accordance with the present invention. For instance, libraries may contain at least 12, 24, 36, 48, 96, 256, 500, 1000, $10^5$, or $10^6$ different materials. In some embodiments, the library can include 96×N different materials, where N ranges from 1 to about 20, and preferably from 1 to about 10 or from 1 to about 5.

By way of illustration, if there is a two ingredient material being prepared, a phase space is formed to examine the complete range of ingredient variation. A first library may be formed by selecting an amount consistent with the size of the region being used (discussed below) and mixing an appropriate molar amount of ingredient A and ingredient B so that the first region of the substrate contains 100% of ingredient A and 0% of ingredient B. The second region may contain 90% of ingredient A and 10% of ingredient B. The third region may contain 80% of ingredient A and 20% of ingredient B. This is repeated until a final region contains 0% of ingredient A and 100% of ingredient B. Library formation in this fashion applies to as many ingredients as desired, including 3 ingredient materials, 4 ingredient materials, 5 ingredient materials, 6 or more ingredient materials, or even 10 or more ingredient materials. Like techniques may be employed in preparing libraries having stoichiometry, thickness or other chemical or physical gradients.

Moreover, in another embodiment of the present invention, a method is provided for forming at least two different libraries of materials by delivering substantially the same ingredients at substantially identical concentrations to regions on both first and second substrates and, thereafter, subjecting the ingredients on the first substrate to a first set of reaction conditions or post-delivery processing or treating conditions and the ingredients on the second substrate to a second set of reaction conditions or post-delivery processing or treating conditions. Using this method, the effects of the various reaction parameters can be studied and, in turn, optimized. Reaction, processing and/or treatment parameters which can be varied include, for example, solvents, temperatures, times, pressures, the atmospheres in which the reactions, processing or treatments are conducted, the rates at which the reactions are quenched, etc. Other reaction or treatment parameters which can be varied will be apparent to those of skill in the art. Hence, one embodiment of the invention is where a library of materials, after its formation, is thereafter subjected to further processing (such as heat treating in an alternative atmosphere) to create an library of different materials.

The library can have as many materials as there are regions on the substrate. For purposes of this invention, the number of materials is typically equal to the number of regions on the substrate, unless certain regions are left empty. The number of regions on the substrate is discussed below, but applies as well to the number of materials.

In some embodiments, a region on the porous substrate is smaller than about 25 cm$^2$, preferably less than 10 cm$^2$, more preferably less than 5 cm$^2$, even more preferably 2 cm$^2$, still more preferably less than 1 cm$^2$, and still more preferably less than 0.5 cm$^2$. In most preferred embodiments, the regions have an area less than about 10,000 $\mu$m$^2$, preferably less than 1,000 $\mu$m$^2$, more preferably less than 100 $\mu$m$^2$, and even more preferably less than 10 $\mu$m$^2$. In this manner, it is possible that relatively small material sample sizes can be employed, such as on the order of about 100 micrograms to about 500 mg, more preferably about 5 to about 50 mg.

Material Handling

As illustrated further (with reference to FIG. 1), delivery of a material to a substrate in accordance with the present invention can be accomplished any of a number of manual or automated methods. One preferred method and system for generating a combinatorial library and performing materials research with the library involves the employment of automated systems driven by suitable software, such as LIBRARY STUDIO™, by Symyx Technologies, Inc. (Santa Clara, Calif.); IMPRESSIONIST™, by Symyx Technologies, Inc. (Santa Clara, Calif.); or a combination thereof. The skilled artisan will appreciate that these systems can be adapted for use in the present invention, taking into account the disclosures set forth in commonly-owned copending U.S. patent application Ser. Nos. 09/174,856 and 09/305,830, each of which is hereby incorporated by reference.

Prior to delivering ingredients, mixing may be desired in preparing material samples or libraries. Mixing is accomplished in any one of many manual or automatic methods. Mixing can be manual such as by shaking the vessel or well. Mixing can also be automatic such as by using an inert ball bearing in a shaken vessel or array of vessels, such as a titer plate. Mixing can also be accomplished via a dispenser that repeatedly aspirates and dispenses some or all of the contents of a vessel or well. In a preferred embodiment, mixing is performed in the nozzle of an automatic dispensing robot that repeatedly aspirates and dispenses some or all of the contents of a vessel or well. Other mixing methods include agitation of the solution with a gas stream, diffusion, sonication or other agitation techniques known to those skilled in the art.

By way of illustration, without limitation, a system for preparing a material sample or library of material samples in accordance with the present invention, includes a container for liquid to be dispensed, a pump system in pumping communication with a valve system. The valve system includes one or more valves (e.g., solenoid valves, such as Microdrop Model 3000 available from BioDot Inc.) adapted so that liquid from the container can be drawn into a dispenser (e.g., a syringe or ink jet dispenser having a nozzle) connected to the valves from negative pressure generated by the pump system. The liquid in the container can then be dispensed onto a substrate, which is preferably held on a mounting surface of a motion plate. In one preferred embodiment, the valve system portion including dispensers is movable in the x, y and z directions and the mounting surface and motion plate is movable in at least the x and y directions, thereby permitting degrees of freedom in the design and creation of spatially addressable material samples in an array. The LIBRARY STUDIO® brand software allows for interface with the pumping system to control dispensing amounts, according to predefined amounts. The IMPRESSIONIST™ brand software in turn controls the translation of the motion plate so that desired compositions or gradients can be prepared at predetermined locations on the substrate.

In some embodiments, the delivery process is repeated to provide materials with as few as two ingredients, although the process may be readily adapted to form materials having 3, 4, 5, 6, or even 10 or more ingredients therein. The density of regions per unit area will be greater than 0.04 regions/cm$^2$, more preferably greater than 0.1 regions/cm$^2$, even more preferably greater than 1 region/cm$^2$, even more preferably greater than 10 regions/cm$^2$, and still more preferably greater than 100 regions/cm$^2$. In most preferred embodiments, the density of regions per unit area will be greater than 1,000 regions/cm$^2$, more preferably 10,000 regions/cm$^2$, and even more preferably greater than 100,000 regions/cm$^2$.

Using the dispenser systems discussed in commonly owned U.S. patent application Ser. No. 08/327,513, incorporated by reference, the individual ingredients or component mixtures can be delivered separately to regions on the substrate either sequentially or simultaneously. In a presently preferred embodiment, the ingredients or component mixtures are sequentially delivered to either a single predefined region on the substrate or, alternatively, to multiple predefined regions on the substrate. For example, using a dispenser having two nozzles, one or more first ingredients can be delivered to regions on the substrate. Alternatively, using this same dispenser, an ingredient can be simultaneously delivered to two different regions on the substrate. In this instance, the same ingredient or, alternatively, two different ingredients can be delivered. If the same ingredient is delivered to both of the regions, it can be delivered at either the same or different concentrations. Similarly, using a dispenser having eight or more nozzles, for example, eight or more different ingredients can be simultaneously delivered to a single region on the substrate or, alternatively, eight or more ingredients (either the same or different) can be simultaneously delivered to eight or more different regions on the substrate.

Other systems may be employed as desired, including automated solid or fluid dispensing systems. For example, the use of a fully automated fluid dispensing system is preferred for use in depositing the material samples of the present invention, which typically will be provided in a liquid medium. Examples of suitable commercially available automated liquid dispensing systems include those offered by CAVRO Scientific Instruments (e.g., Model NO. RSP9652) or BioDot (Microdrop Model 3000). The fluids delivered by any dispensing technique will be introduced through passageways of the material sample collector described herein. Thereafter, a suitable negative pressure may be applied to flow the fluid through a porous substrate, where solids will be captured and retained for later treatment, testing or both.

It will be appreciated that liquid dispensing as used in the present invention affords a number of unique advantages. For instance, it is generally possible to add surfactants or other agents to the liquids to assist in controlling spreading of the film. Droplet volume control is also possible. However, from application to application, the skilled artisan will appreciate that some minor predictions, trial and error or both may be appropriate for achieving the desired result depending upon any additives employed, the solvent selected, the concentration, the temperature, the evaporation rate, the class of material being deposited or the like.

It will be appreciated that the practice of the present invention need not include each of the above components or steps. Components or steps can be combined or omitted as desired. Further, it is possible that the system may be an integrated assembly of some or all of the components, or the components may be configured as discrete stand-alone components.

Molding or shaping may be accomplished using any other art-disclosed molding technique, including but not limited to injection molding, solution film casting, capillary extrusion, or the like. Additionally, bulk shapes can be molded using art-disclosed techniques and then machined or otherwise processed to the final desired shape.

The preparation and dispensing of material samples having been discussed in detail in the above, and otherwise employing art-disclosed techniques, the discussion now turns to the particular material sample collector and preferred analytical instrument.

Automation

Though manual methods are possible, in a particularly preferred embodiment, the preparation and analysis of material samples is performed in at least a partially automated manner, and is facilitated by the use of suitable software. Though it is possible that several functions may be combined into an integrated software package, it is anticipated that the software will likely be packaged as separate modules, or as a group of separate modules together in a suite. Though any suitable software may be employed, preferred software is that available from Symyx Technologies, Inc. (Sunnyvale, Calif.), under the designations identified parenthetically in the following discussion.

Figure 15:
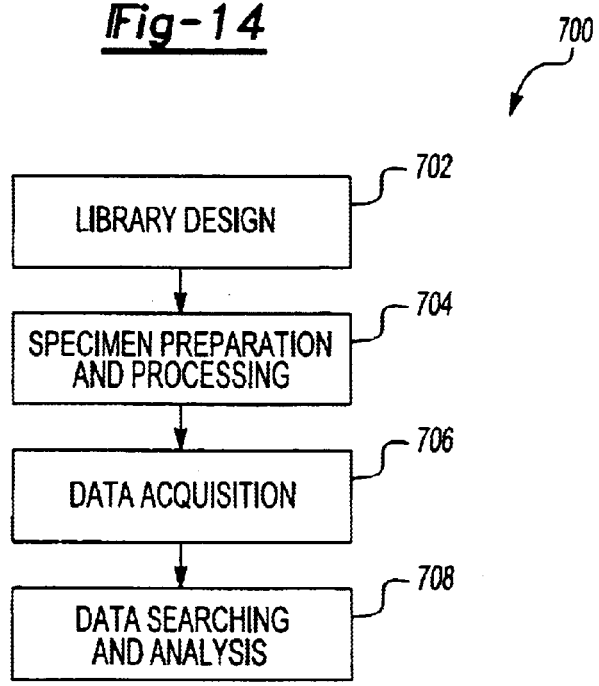
FIG. 15 illustrates a flowchart of an exemplary set of steps that may be used for processing material sample according to an aspect of the present invention.

In general, software is employed in at least the following processing steps that are indicated in the flowchart of FIG. 15:

1) designing a library (e.g., LIBRARY STUDIO™) as indicated by the first block 702 of the flowchart 700
2) translating a library design into commands for directing robots or other instrumentation to prepare material samples and thereafter process them (e.g., IMPRESSIONIST™) as indicated by the second block 704 of the flowchart 700
3) acquiring data about material samples in a library (e.g., EPOCH™) as indicated by the third block 706 of the flowchart 700; and
4) organizing and displaying material sample data for search or analysis (e.g., POLY VIEW™) as indicated by the fourth block 708 of the flowchart 700.

A more detailed discussion of the features and operation of sample preparation or processing software can be found in U.S. patent application Ser. Nos. 09/420,334 (filed Oct. 18, 1999); Ser. No. 09/174,856 (filed Oct. 19, 1998); 09/305, 830 (filed May 5, 1999), incorporated by reference herein.

Further, it is also contemplated that any suitable commercially available software will be employed for storing and retrieving material sample data (e.g., database software available from ORACLE), correlating material sample data with information about a material sample or other material samples in a library, or both. For example, for each material sample, the information obtained preferably is inputted and stored into a computer, which can retrieve such information for subsequent analysis or comparison with other library members.

By way of further background, in the context of the present invention, preferably library design will employ software including graphical user interface for designing a library. The software may provide a navigational interface pane for permitting a user to access, view and edit a design of a particular library (including information about its constituent members, such as composition). The software preferably provides a formatted work pane for prompting a user to input data about desired characteristics of a library member. The software also preferably provides a formatted definition pane, pursuant to which users are prompted to define or specify stock materials, chemical concentrations, reaction conditions or the like. The software is capable if storing such data once inputted. In this manner, by way of example, a user is able to design a library of reagent formulations or synthesis products by mapping gradients across a matrix (e.g., by amount such as volume); alternatively, individual or subsets of cells can be mapped within one or more plates across a matrix using equations (e.g., by volume, mass, moles, mmoles, mole/l, mmole/l or the like). Preferably the software allows for the input of data for design of a single library or a plurality of libraries, as might span across multiple physical plates.

It will also be appreciated that in the design of an experiment, composition need not be the only variable within a library, or across plural libraries. Other variables include, without limitation, addition sequence, addition time, addition rate, temperature history, mixing type, mixing speed, mixing torque, shear strain, elongational strain, mixing history, cure history, environment, residence time distribution or the like. In a preferred embodiment, an experiment is performed with varying composition. In another preferred embodiment, an experiment is performed with a common composition at and variation of at least one, and preferably two, more preferably three, and still more preferably four or more of the above variables. In yet another preferred embodiment, an experiment is performed with a varying composition at and variation of at least one, and preferably two, and more preferably three, and still more preferably four or more of the above variables.

As indicated, it is desirable to automate library preparation by employing suitable software for translating a library design into commands for directing robots or other instrumentation to prepare material samples and thereafter process them. In general, this software will interface between the library design software and the automated instruments that are used for preparing the libraries. Thus, the software will translate data inputted for a particular library member or members into a signal for assisting in controlling the automated instruments. By way of example, data inputted for the design of a proposed library member might require that a first component and a second component, both the first and second components being kept at separate sites, be dispensed in certain proportions onto a common region of substrate. Preferably the present software will direct an instrument, such as a material sample handling robot (e.g., a CAVRO™ robot), to translate one or more dispensers to collect the first component and the second components and deliver them to the designated region of the substrate. Likewise, the software preferably permits for controlling post-deposition processing or possibly analysis (or material sample processing where there has been no deposition), in like manner. Suitable software is also employed for assisting in the performance of material sample analysis, such as for instance the high throughput testing or characterization of a material sample.

Data Analysis

Another aspect of the present invention involves correlating the data received from the material sample analysis or other screen with information known about ingredients of each of the materials, processing conditions of each of the materials or a combination thereof. The respective material samples of one or more libraries can be compared with each other based upon the data and ranked. In this manner, a large field of research candidates can be narrowed to a smaller field by identifying the candidates that perform better than others with respect to a predetermined property structure, or figure of merit. Comparative review of results might lead to rankings of performance from better to worse, or the like. Likewise, a large field of research candidates can be narrowed to a smaller one by identifying those that meet a certain predetermined criteria. Additional libraries can then be prepared for further analysis. Alternatively, bulk quantities of materials having the desired properties or structures can be made for commercial applications. Data analysis may be performed manually, or by semi-automated or automated techniques. For example, it is possible to employ either or both of the LIBRARY STUDIO® (from Symyx Technologies, Inc.) and IMPRESSIONIST™ (from Symyx Technologies, Inc.) for library design and synthesis, and POLYVIEW™ (from Symyx Technologies, Inc.) or other suitable data management software to assist in correlating the data. Further, it is contemplated that data obtained from the use of the present invention can be used to develop data bases, such as a crystallography data base, or can be used for further interpretation or modeling.

It will be appreciated that the correlating protocol may be executed by suitable software. For instance, much of the above information typically will be inputted into a computer in the course of designing a library, (e.g. using software such as previously described LIBRARY STUDIO®)), or in the course of programming or otherwise directing an instrument for exercising an operation upon a material (e.g. through the use of software such as IMPRESSIONIST™).

In this manner it is possible to store, retrieve, organize or otherwise manage information about many material samples.

Further it is possible to analyze trends of different materials, or plural material samples of the same material that has been subjected to different processing parameters or other conditions. An entire design space may be analyzed rapidly.

Figure 16:
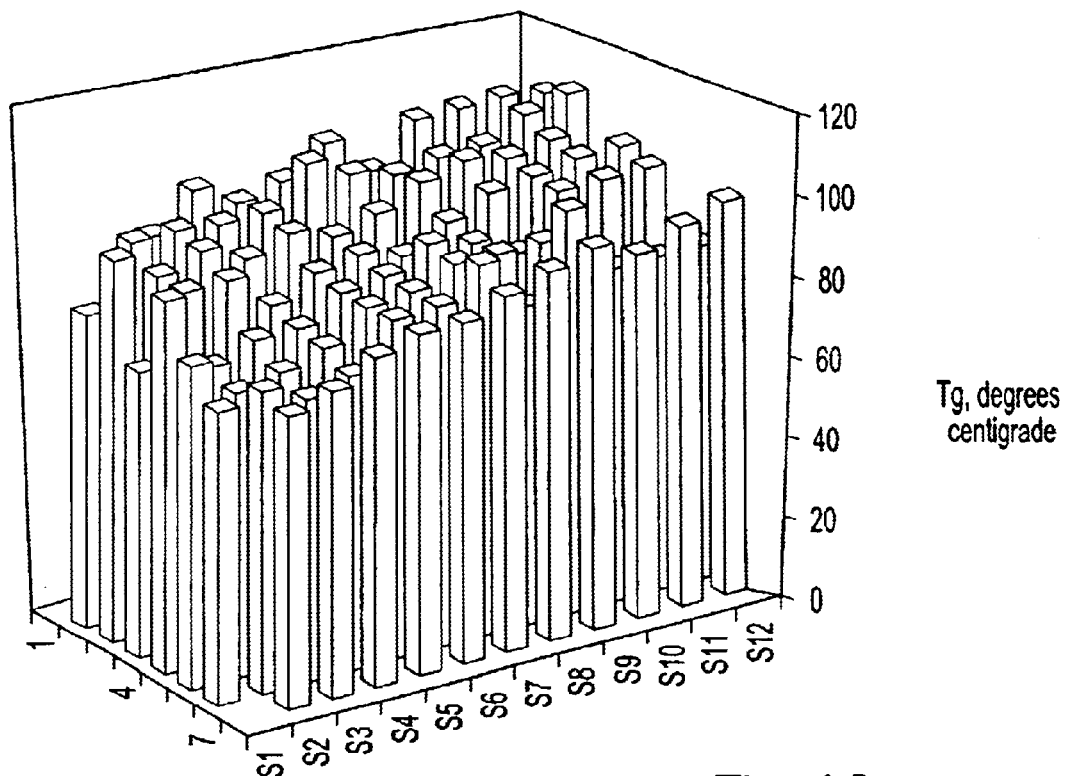
FIG. 16 illustrates a graphical representation of data acquired for material samples according to an aspect of the present invention.

Preferably, the information is outputted for visual analysis in, for example, two or three dimensional format. Without limitation, one example of such output is illustrated in FIG. 16, which plots sample variable vs. base sample vs. temperature such that the glass transition temperatures of the samples may be identified. Trends can readily be analyzed within a single plot, or alternatively among different plots. In one embodiment, the plot may include only material samples from a single library. In another embodiment the plot includes material samples from different libraries, or the results address a property other than Tg.

Relative material sample comparisons may be made form analyzing individual data points, or the data point may be confined to an analysis of whether a certain predetermined condition has been met. Materials may then be ranked according to the respective information known about them.

By way of illustration, suppose a library has five material samples (or a multiple thereof). For illustration purposes, each material sample is different from each other material sample by the relative concentrations of their ingredients A and B (of course one or more other variables might be used instead of concentration) according to Table I.

| Material sample | A | B | Crystalline (yes/no) | Mechanical Property | Mechanical Property Rank |
|---|---|---|---|---|---|
| 1 | 0 | 100 | No | 100 | 3 |
| 2 | 25 | 75 | No | 110 | 2 |
| 3 | 50 | 50 | Yes | 150 | 1 |
| 4 | 75 | 25 | Yes | 70 | 4 |
| 5 | 100 | 0 | No | 60 | 5 |

As can be seen, relative performance of material samples may be compared and evaluated such as by determining whether the materials satisfy a predetermined criteria or by possibly comparing the specific quantitative data observed from analysis of the materials.

It may also be possible to store the information about a library for future retrieval (e.g. more than one day, one week, one month, or even one year after characterization). Materials that do not meet a specified characteristic in the present may thereafter meet such specification. For example, referring to the Table I, it may be determined at some future date that a need exists for a blend of A and B that is crystalline but does not have a mechanical property amount greater than 75. A query of a database including the information of Table I would identify Material sample 4 as meeting this criteria. Information about the concentration or other parameters of Material sample 4 could be retrieved and the material further analyzed.

Under any approach, it is also contemplated specifically that materials that satisfy certain criteria, perform better than others for a desired location or a combination thereof, can be identified for further study. Such further study might include further material sample preparation and screening, the preparation of pilot- or bench-scale quantities or even the preparation of bulk quantities, (e.g. an amount sufficient to meet the demand of an industrial-scale application, for instance, such as a commercial application where the material is to be processed into useful or salable article). Depending upon the intended application, a bulk quantity may be as small as 1 kg or less, but typically will be larger than about 10 kg, more preferably larger than about 100 kg and still more preferably larger than about 1000 kg and still more preferably greater than about 10,000 kg.

Throughput

Throughputs obtainable according to the present invention preferably are high, and more preferably are higher than other art disclosed methods. Throughput will depend upon any of a number of different factors, including but not limited to the number of material samples in a library. The size of the material samples, the number of different characterizations performed upon given material sample or the like. Assuming individual material sample sizes less than 0.2 kg, in one highly preferred embodiment, a material sample or library of material samples is prepared and characterized for only one of morphology, size, physical property or mechanical property. Though other results are possible with the present invention, preferably material sample preparation throughput averages no more than about 8 hours per material sample, more preferably no ore than about 4 hours per material sample, still more preferably no more than about one hour per material sample, and even still more preferably no more than about 0.25 hour per material sample, and even still more preferably no more than about 0.1 hour per sample.

For an embodiment in which a material sample or library of material samples is prepared and characterized for two or more of morphology, size, physical property or mechanical property, material sample throughput averages no more than about 12 hours per material sample, more preferably no more than about 6 hours per material sample, still more preferably no more than about 1.5 hours per material sample, and even still more preferably no more than about 0.4 hours per material sample.

From the above, it will be readily appreciated how the present invention advantageously is employed in the rapid preparation and analysis of one or a plurality of new but uncharacterized blend materials. The invention may also be employed for the rapid analysis of existing known blend materials. In another embodiment, a combination of known and unknown materials (e.g., blend materials) are rapidly prepared or analyzed, such as by the use of a reference control or standard in a library of materials.

Throughputs may also be made more efficient through the employment of commercially available technology from Symyx Technologies, Inc., such as the PPR™ polymerization reactor technology, for the preparation of polymers.

The invention has been described with particular reference to preferred embodiments thereof, variations and modifications can be effected within the spirit and scope of the following claims.

What is claimed is:

1. A method for high throughput preparation and screening of blend materials, comprising the steps of:
   (a) providing a first polymer material;
   (b) providing at least one additional material;
   (c) blending said at least one additional material to form a blend with said first polymer material;
   (d) forming a miniature material sample of said blend to a desired sample shape;
   (e) characterizing said blend as to morphology, size, composition, property or a combination thereof;
   (f) repeating said steps (a)–(e) for forming and characterizing a plurality of material samples of a library of material samples; and
   (g) preparing at least one additional sample based upon information obtained from steps (a)–(f).

2. The method of claim 1, wherein said resulting blend includes at least three different polymer materials.

3. The method of claim 1, wherein the materials of said blend are compositionally the same but differ in architecture.

4. The method of claim 1, wherein the materials of said blend are compositionally the same but differ in polydispersity.

5. The method of claim 1, wherein said at least one additional material is an inorganic material.

6. The method of claim 1, wherein at least one of said materials is provided in a liquid state and said liquid state is selected from a molten state or a dissolved state.

7. The method of claim 1, wherein said first polymer material is provided by an automated dispenser in a dissolved state.

8. The method of claim 1, wherein said material sample is smaller than about 0.1 kg.

9. The method of claim 8, wherein said step (f) is repeated to form a library of at least about 24 samples.

10. The method of claim 1, wherein at least one of said step (e) or said step (f) is conducted simultaneously for a plurality of samples.

11. The method of claim 1, wherein the blending is at least partially performed by a technique selected from melt blending, liquid blending or a combination thereof.

12. The method of claim 1, wherein the blending is performed in a device selected from a miniature extruder, a calendar mill or a rotary mixer.

13. The method of claim 1, wherein the sample is formed by a technique selected from molding, compression of a material sample between opposing surfaces, contact with a roller surface having a predefined topography, microcentrifugation or a combination thereof.

14. The method of claim 1 wherein step (c) is performed in a plural screw extruder and the repeating of step (c) is performed simultaneously by melt blending each said first polymer material with each said at least one additional material using a different screw of the plural screw extruder to form each blend.

15. The method of claim 1 wherein step (c) is performed with a milling apparatus that includes multiple roller assemblies, each assembly having a first roller and a second roller and wherein the repeating of step (c) is performed simultaneously by melt blending each said first polymer material with each said at least one additional material using a different roller assembly of the multiple roller assemblies to form each blend.

16. The method of claim 1 wherein step (c) and step (d) are performed in a substrate having multiple wells and multiple pistons and wherein the repeating of step (c) and (d) is performed by compressing each said first polymer material with each said at least one additional material in a different well of the multiple wells using a different piston of the multiple pistons to form each sample.

17. The method of claim 1 wherein step (c) is performed with a rotary mixing apparatus that includes multiple rotor shafts and wherein the repeating of step (c) is performed simultaneously by mixing each said first polymer material with each said at least one additional material using a different rotor shaft of the multiple rotor shafts to form each blend.

18. The method of claim 1 wherein step (d) is performed with a rotating microcentrifugation tool that includes multiple radial wells and wherein the repeating of step (d) is performed by dispensing each said first polymer material with each said at least one additional material into a different radial well as the rotating tool rotates to form each sample.

19. The method of claim 1 wherein step (d) is performed by supplying each said first polymer material and each said at least one additional material to one or more molds either simultaneously or serially for forming the plurality of samples.

20. The method of claim 1 wherein said first polymer material is selected from a polyolefin, a polyethylene, a polypropylene, a polyethylene terephthalate, a vinyl, a polyvinyl chloride, a polyamide, a polyimide, a polyurethane, an acrylic, a polyester, a cellulose, an acetate, a melamine, a thermoplastic rubber, a thermosetting rubber, a fluorocarbon, a polytetrafluoroethylene, a polystyrene, a nitrile, a phenolic, a polycarbonate, an epoxy, an acrylonitrilebutadienestyrene, a polyethylene ether ketone, an acetal or a combination thereof.

21. The method of claim 1 wherein the desired shaped of the sample is selected from circular, cylindrical, rectangular, block, annular, square or a combination thereof.

22. The method of claim 1 wherein step (e) employs a techniques selected from beam radiation analysis, x-ray diffraction, high-throughput x-ray scattering, scattering from experimental systems, viscometry, failure or strength testing, adhesion testing, birefrigerance, rheo-optics, electron radiation, neutron radiation, synchotron radiation, infrared techniques, thermal analysis techniques, chromatographic techniques, resonance, spectroscopy, light scatter, spectrometry, microscopy, nuclear magnetic resonance, optical measurements, electrochemical measurements or a combination thereof.

23. A method for high throughput preparation and screening of blend materials, comprising the steps of:
(a) providing a first polymer material;
(b) providing at least one additional polymer material;
(c) blending said at least one additional polymer material to form a blend with said first polymer material;
(d) forming a miniature material sample of said blend to a desired sample shape;
(e) characterizing said blend as to morphology, size, composition, property or a combination thereof;
(f) repeating said steps (a)–(e) for forming and characterizing a plurality of material samples of a library of material samples;
(g) correlating the results of said steps (a)–(f) with known information about each said blend; and
(h) preparing at least one additional sample based upon information obtained from said steps (a)–(g).

24. The method of claim 23, wherein said material sample is smaller than about 0.01 kg.

25. The method of claim 24, wherein said step (f) is repeated to form a library of at least about 24 samples.

26. The method of claim 23, wherein at least one of said characterizing steps (g)–(h) is performed simultaneously for all samples in said library.

27. The method of claim 23, wherein at least one of said step (e) or said step (f) is conducted simultaneously for a plurality of samples.

28. The method of claim 23, wherein the blending is at least partially performed by a technique selected from melt blending, liquid blending or a combination thereof.

29. The method of claim 23, wherein the blending is performed in a device selected from a miniature extruder, a calendar mill or a rotary mixer.

30. The method of claim 23, wherein the sample is formed by a technique selected from molding, compression of a material sample between opposing surfaces, contact with a roller surface having a predefined topography, microcentrifugation or a combination thereof.

31. The method of claim 23 wherein step (c) is performed in a plural screw extruder and the repeating of step (c) is performed simultaneously by melt blending each said first polymer material with each said at least one additional material using a different screw of the plural screw extruder to form each blend.

32. The method of claim 23 wherein step (c) is performed with a milling apparatus that includes multiple roller assemblies, each assembly having a first roller and a second roller and wherein the repeating of step (c) is performed simultaneously by melt blending each said first polymer material with each said at least one additional material using a different roller assembly of the multiple roller assemblies to form each blend.

33. The method of claim 23 wherein step (c) and step (d) are performed in a substrate having multiple wells and multiple pistons and wherein the repeating of step (c) and (d) is performed by compressing each said first polymer material with each said at least one additional material in a different well of the multiple wells using a different piston of the multiple pistons to form each sample.

34. The method of claim 23 wherein step (c) is performed with a rotary mixing apparatus that includes multiple rotor shafts and wherein the repeating of step (c) is performed simultaneously by mixing each said first polymer material with each said at least one additional material using a different rotor shaft of the multiple rotor shafts to form each blend.

35. The method of claim 23 wherein step (d) is performed with a rotating microcentrifugation tool that includes multiple radial wells and wherein the repeating of step (d) is performed by dispensing each said first polymer material with each said at least one additional material into a different radial well as the rotating tool rotates to form each sample.

36. The method of claim 23 wherein step (d) is performed by supplying each said first polymer material and each said at least one additional material to one or more molds either simultaneously or serially for forming the plurality of samples.

37. The method of claim 23 wherein said first polymer material is selected from a polyolefin, a polyethylene, a polypropylene, a polyethylene terephthalate, a vinyl, a polyvinyl chloride, a polyamide, a polyimide, a polyurethane, an acrylic, a polyester, a cellulose, an acetate, a melamine, a thermoplastic rubber, a thermosetting rubber, a fluorocarbon, a polytetrafluoroethylene, a polystyrene, a nitrile, a phenolic, a polycarbonate, an epoxy, an acrylonitrilebutadienestyrene, a polyethylene ether ketone, an acetal or a combination thereof.

38. The method of claim 23 wherein the desired shaped of the sample is selected from circular, cylindrical, rectangular, block, annular, square or a combination thereof.

39. The method of claim 23 wherein step (e) employs a techniques selected from beam radiation analysis, x-ray diffraction, high-throughput x-ray scattering, scattering from experimental systems, viscometry, failure or strength testing, adhesion testing, birefrigerance, rheo-optics, electron radiation, neutron radiation, synchotron radiation, infrared techniques, thermal analysis techniques, chromatographic techniques, resonance, spectroscopy, light scatter, spectrometry, microscopy, nuclear magnetic resonance, optical measurements, electrochemical measurements or a combination thereof.

40. A method for high throughput preparation and screening of materials, comprising the steps of:
(a) providing a polymer material;
(b) forming a miniature material sample of said polymer material to a desired sample shape;
(c) characterizing said sample as to morphology, size, composition, property or a combination thereof;
(d) repeating said steps (a)–(c) for forming and characterizing a plurality of material samples of a library of material samples;
(e) correlating the results of said steps (a)–(d) with known information about each said material sample; and
(f) preparing at least one additional sample based upon information obtained from said steps (a)–(e).

41. The method of claim 40, wherein the samples are compositionally the same but differ in architecture.

42. The method of claim 40, wherein the samples are compositionally the same but differ in polydispersity.

43. The method of claim 40, wherein said polymer material is provided in a liquid state and said liquid state is selected from a molten state or a dissolved state.

44. The method of claim 40, wherein said material sample is smaller than about 0.1 kg.

45. The method of claim 40, wherein said step (d) is repeated to form a library of at least about 24 samples.

46. The method of claim 40, wherein at least one of said steps (e)–(f) is performed simultaneously for all samples in said library.

47. The method of claim 40, wherein at least one of said step (c) or said step (d) is conducted simultaneously for a plurality of samples.

48. A method for high throughput preparation and screening of materials, comprising the steps of:
(a) providing a polymer blend;
(b) forming a miniature material sample of said blend to a desired sample shape;
(c) characterizing said sample as to morphology, size, composition, property or a combination thereof said characterizing step including a step of adhesion testing;
(d) repeating said steps (a)–(c) for forming and characterizing a plurality of material samples of a library of material samples;
(e) correlating the results of said steps (a)–(d) with known information about each said blend; and
(f) preparing at least one additional sample based upon information obtained from steps (a–(e).

49. The method of claim 48, wherein said polymer blend is provided in a liquid state and said liquid state is selected from a molten state or a dissolved state.

50. The method of claim 48 wherein step (c) further employs a techniques selected from beam radiation analysis, x-ray diffraction, high-throughput x-ray scattering, scattering from experimental systems, viscometry, failure or strength testing, birefrigerance, rheo-optics, electron radiation, neutron radiation, synchotron radiation, infrared techniques, thermal analysis techniques, chromatographic techniques, resonance, spectroscopy, light scatter, spectrometry, microscopy, nuclear magnetic resonance, optical measurements, electrochemical measurements or a combination thereof.

51. The method of claim 48 wherein said polymer blend includes an acrylic.

52. The method of claim 48 wherein said steps (a)–(c) are preformed on a flexible substrate.

53. The method of claim 48 wherein said polymer blend is provided in a liquid state, through an automated dispenser, onto a flexible substrate resulting in a material sample smaller than about 0.1 kg.

54. The method of claim 53 wherein said polymer blend includes an acrylic, said blend is dispensed, in a liquid state using an automated dispenser, onto a flexible substrate resulting in a material sample smaller than about 0.1 kg, and wherein said characterizing of said blend further comprises adhesion testing.

55. The method of claim 54 further comprising a step of preparing a bulk material based upon the results of said steps (a)–(e).

56. The method of claim 48 further comprising a step of preparing a bulk material based on the results of said steps (a)–(e).

* * * * *